United States Patent
Boehm et al.

(10) Patent No.: US 12,241,830 B2
(45) Date of Patent: Mar. 4, 2025

(54) LIVING BIOSENSORS

(71) Applicant: The Broad Institute, Inc., Cambridge, MA (US)

(72) Inventors: Jesse Boehm, Cambridge, MA (US); Niklas Rindtorff, Cambridge, MA (US); JT Neal, Cambridge, MA (US); Aviad Tsherniak, Cambridge, MA (US); Mushriq Muhib Al-Jazrawe, Cambridge, MA (US)

(73) Assignee: Broad Institute, Inc., Cambridge, MA (US)

( * ) Notice: Subject to any disclaimer, the term of this patent is extended or adjusted under 35 U.S.C. 154(b) by 470 days.

(21) Appl. No.: 17/113,790

(22) Filed: Dec. 7, 2020

(65) Prior Publication Data
US 2021/0190762 A1 Jun. 24, 2021

Related U.S. Application Data

(60) Provisional application No. 62/944,880, filed on Dec. 6, 2019.

(51) Int. Cl.
*G01N 33/48* (2006.01)
*G01N 21/64* (2006.01)
*G01N 33/50* (2006.01)

(52) U.S. Cl.
CPC ......... *G01N 21/64* (2013.01); *G01N 21/6458* (2013.01); *G01N 21/6486* (2013.01); *G01N 33/5023* (2013.01); *G01N 33/5026* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 5,013,830 A | 5/1991 | Ohtsuka et al. | |
| 5,030,015 A | 7/1991 | Baker et al. | |
| 5,149,797 A | 9/1992 | Pederson et al. | |
| 5,220,007 A | 6/1993 | Pederson et al. | |
| 5,256,775 A | 10/1993 | Froehler | |
| 5,366,878 A | 11/1994 | Pederson et al. | |
| 5,403,711 A | 4/1995 | Walder et al. | |
| 5,491,133 A | 2/1996 | Walder et al. | |
| 5,565,350 A | 10/1996 | Kmiec | |
| 5,623,065 A | 4/1997 | Cook et al. | |
| 5,652,355 A | 7/1997 | Metelev et al. | |
| 5,652,356 A | 7/1997 | Agrawal | |
| 5,700,922 A | 12/1997 | Cook | |
| 6,479,626 B1 | 11/2002 | Kim et al. | |
| 6,534,261 B1 | 3/2003 | Cox et al. | |
| 6,607,882 B1 | 8/2003 | Cox et al. | |
| 6,746,838 B1 | 6/2004 | Choo et al. | |
| 6,794,136 B1 | 9/2004 | Eisenberg et al. | |
| 6,824,978 B1 | 11/2004 | Cox et al. | |
| 6,866,997 B1 | 3/2005 | Choo et al. | |
| 6,903,185 B2 | 6/2005 | Kim et al. | |
| 6,933,113 B2 | 8/2005 | Case et al. | |
| 6,979,539 B2 | 12/2005 | Cox et al. | |
| 7,013,219 B2 | 3/2006 | Case et al. | |
| 7,030,215 B2 | 4/2006 | Liu et al. | |
| 7,220,719 B2 | 5/2007 | Case et al. | |
| 7,241,573 B2 | 7/2007 | Choo et al. | |
| 7,241,574 B2 | 7/2007 | Choo et al. | |
| 7,585,849 B2 | 9/2009 | Liu et al. | |
| 7,595,376 B2 | 9/2009 | Kim et al. | |
| 8,021,867 B2 | 9/2011 | Smith et al. | |
| 8,119,361 B2 | 2/2012 | Smith et al. | |
| 8,119,381 B2 | 2/2012 | Smith et al. | |
| 8,124,369 B2 | 2/2012 | Smith et al. | |
| 8,129,134 B2 | 3/2012 | Smith et al. | |
| 8,133,697 B2 | 3/2012 | Smith et al. | |
| 8,163,514 B2 | 4/2012 | Smith et al. | |
| 8,604,192 B2 | 12/2013 | Seth et al. | |
| 8,697,663 B2 | 4/2014 | Bennett et al. | |
| 8,703,728 B2 | 4/2014 | Swayze et al. | |
| 8,796,437 B2 | 8/2014 | Swayze et al. | |
| 8,865,677 B2 | 10/2014 | Manoharan et al. | |
| 8,883,752 B2 | 11/2014 | Swayze et al. | |
| 2014/0297199 A1* | 10/2014 | Osten ................. | G01N 33/5008 435/7.1 |
| 2016/0060691 A1 | 3/2016 | Giresi et al. | |
| 2016/0208323 A1 | 7/2016 | Bernstein et al. | |
| 2019/0012521 A1* | 1/2019 | Cohen .................... | G16B 40/20 |

FOREIGN PATENT DOCUMENTS

| | | |
|---|---|---|
| WO | 2010/040112 A2 | 4/2010 |
| WO | 2014/093622 A2 | 6/2014 |
| WO | 2014/210353 A2 | 12/2014 |

(Continued)

OTHER PUBLICATIONS

Levy, Angela D., Janet C. Shaw, and Leslie H. Sobin. "Secondary tumors and tumorlike lesions of the peritoneal cavity: imaging features with pathologic correlation." Radiographics 29.2 (2009): 347-373.*

Eilken, Hanna M., Shin-Ichi Nishikawa, and Timm Schroeder. "Continuous single-cell imaging of blood generation from haemogenic endothelium." Nature 457.7231 (2009): 896-900.*

Heo, Young Jin, et al. "Real-time image processing for microscopy-based label-free imaging flow cytometry in a microfluidic chip." Scientific reports 7.1 (2017): 11651.*

.Chen, Claire Lifan, et al. "Deep learning in label-free cell classification." Scientific reports 6.1 (2016): 21471.*

Kobayashi, Hirofumi, et al. "Label-free detection of cellular drug responses by high-throughput bright-field imaging and machine learning." Scientific reports 7.1 (2017): 12454.*

(Continued)

*Primary Examiner* — Anna Skibinsky
(74) *Attorney, Agent, or Firm* — F. Brent Nix, Esq.; Johnson, Marcou, Isaacs & Nix; Cheri Arnsdorff

(57) ABSTRACT

Ex vivo cell-based living biosensors, methods of imaging and identifying cell types and/or cell phenotypes, and uses of the systems and methods are provided.

20 Claims, 2 Drawing Sheets
Specification includes a Sequence Listing.

(56) References Cited

FOREIGN PATENT DOCUMENTS

| | | |
|---|---|---|
| WO | 2015/130968 A2 | 9/2015 |
| WO | 2016/040476 A1 | 3/2016 |
| WO | 2016/168584 A1 | 10/2016 |
| WO | 2017/156336 A1 | 9/2017 |
| WO | 2017/164936 A1 | 9/2017 |
| WO | 2018/213708 A1 | 11/2018 |
| WO | 2018/213726 A1 | 11/2018 |
| WO | 2019/005884 A1 | 1/2019 |
| WO | 2019/005886 A1 | 1/2019 |
| WO | 2019/018423 A1 | 1/2019 |
| WO | 2019/060746 A1 | 3/2019 |
| WO | 2019/071048 A1 | 4/2019 |
| WO | 2019/094984 A1 | 5/2019 |
| WO | 2019/126709 A1 | 6/2019 |
| WO | 2019/126716 A1 | 6/2019 |
| WO | 2019/126762 A2 | 6/2019 |
| WO | 2020/033601 A1 | 2/2020 |
| WO | 2020/077236 A1 | 4/2020 |
| WO | 2020/131862 A1 | 6/2020 |

OTHER PUBLICATIONS

Burnett, et al., "RNA-Based Therapeutics: Current Progress and Future Prospects", Chemistry & Biology, vol. 19, No. 1, Jan. 27, 2012, 60-71.

Caicedo, et al., "Weakly Supervised Learning of Single-Cell Feature Embeddings", Proceedings of the IEEE Conference on Computer Vision and Pattern Recognition (CVPR), 2018, 9309-9318.

Cao, et al., "Comprehensive Single Cell Transcriptional Profiling of a Multicellular Organism by Combinatorial Indexing", Available at: BioRxiv https://doi.org/10.1101/104844, Feb. 2, 2017, 35 pages.

Cao, et al., "Comprehensive Single-cell Transcriptional Profiling of a Multicellular Organism", Science, vol. 357, No. 6352, Aug. 18, 2017, 661-667.

Christiansen, et al., "In Silico Labeling: Predicting Fluorescent Labels in Unlabeled Images", Cell, vol. 173, Issue 3, Apr. 19, 2018, 792-803.

Drokhlyansky, et al., "The Human and Mouse Enteric Nervous System at Single-Cell Resolution", Cell, vol. 182, No. 6, 2020, 1606-1622.

Gierahn, et al., "Seq-Well: Portable, Low-Cost RNA Sequencing of Single Cells at High Throughput", Nature Methods, vol. 14, No. 4, Apr. 2017, 8 pages.

Habib, et al., "Div-Seq: Single-Nucleus RNA-Seq Reveals Dynamics of Rare Adult Newborn Neurons", Science, vol. 353, No. 6302, Aug. 26, 2016, 925-928.

Habib, et al., "Massively Parallel Single-Nucleus RNA-seq with DroNc-seq", Nature Methods, vol. 14, No. 10, Oct. 2017, 18 pages.

Hughes, et al., "Highly Efficient, Massively-Parallel Single-Cell RNA-Seq Reveals Cellular States and Molecular Features of Human Skin Pathology", Retrieved as on Jun. 10, 2020:-https://doi.org/10.1101/689273, Jul. 2, 2019, 51 pages.

Klein, et al., "Droplet Barcoding for Single-Cell Transcriptomics Applied to Embryonic Stem Cells", Cell, vol. 161, No. 6, May 21, 2015, 1187-1201.

Lagos-Quintana, et al., "Identification of Novel Genes Coding for Small Expressed RNAs", Science, vol. 294, No. 5543, Oct. 26, 2001, 853-858.

Lagos-Quintana, et al., "Identification of Tissue-Specific MicroRNAs from Mouse", Current Biology, vol. 12, No. 9, Apr. 30, 2002, 735-739.

Lagos-Quintana, et al., "New MicroRNAs from Mouse and Human", RNA, vol. 9, No. 2, Feb. 9, 2003, 175-179.

Lamb, Justin, "The Connectivity Map: A New Tool for Biomedical Research", Nature Reviews Cancer, vol. 7, No. 1, Jan. 2007, 54-60.

Lamb, et al., "The Connectivity Map: Using Gene-Expression Signatures to Connect Small Molecules, Genes, and Disease", Science, vol. 313, Issue 5795, Sep. 29, 2006, 1929-1935.

Lau, et al., "An Abundant Class of Tiny RNAs with Probable Regulatory Roles in Caenorhabditis Elegans", Science, vol. 294, No. 5543, Oct. 26, 2001, 858-862.

Lee, et al., "An Extensive Class of Small RNAs in Caenorhabditis Elegans", Science, vol. 294, No. 5543, Oct. 26, 2001, 862-864.

Lim, et al., "The MicroRNAs of Caenorhabditis Eegans", Genes & Development, vol. 17, No. 8, Apr. 15, 2003, 991-1008.

Lim, et al., "Vertebrate MicroRNA Genes", Science, vol. 299, No. 5612, Mar. 7, 2003, 1540 page.

Macosko, et al., "Highly Parallel Genome-wide Expression Profiling of Individual Cells Using Nanoliter Droplets", Cell 161, No. 6, May 21, 2015, 1202-1214.

Ounkomol, et al., "Label-Free Prediction of Three-Dimensional Fluorescence Images from Transmitted-Light Microscopy", Nature Methods, vol. 15, 2018, 917-920.

Rosenberg, et al., "Scaling Single Cell Transcriptomics Through Split Pool Barcoding", Available at:Bio Rxiv http://dx.doi.org/10.1101/105163, Feb. 2, 2017, 13 pages.

Rosenberg, et al., "Single-Cell Profiling of the Developing Mouse Brain and Spinal Cord with Split-Pool Barcoding", Science, vol. 360, No. 6385, Mar. 15, 2018, 8 pages.

Swiech, et al., "In Vivo Interrogation of Gene Function in the Mammalian Brain Using CRISPR-Cas9", Nature Biotechnology, vol. 33, No. 1, 2014, 102-106.

Vitak, et al., "Sequencing Thousands of Single-Cell Genomes with Combinatorial Indexing", Nature Methods, vol. 14, No. 3, Mar. 2017, 302-308.

Wagner, et al., "Revealing the Vectors of Cellular Identity with Single-Cell Genomics", Nature Biotechnology, vol. 34, No. 11, 2016, 1145-1160.

Zheng, et al., "Haplotyping Germline and Cancer Genomes with High-Throughput Linked-Read Sequencing", Nature Biotechnology, vol. 34, No. 3, Mar. 2016, 303-311.

Zheng, et al., "Massively Parallel Digital Transcriptional Profiling of Single Cells", Nature Communications, vol. 8, No. 14049, Jan. 16, 2017, 12 pages.

Zilionis, et al., "Single-cell Barcoding and Sequencing Using Droplet Microfluidics", Nature Protocols, vol. 12, No. 1, Jan. 2017, 44-73.

* cited by examiner

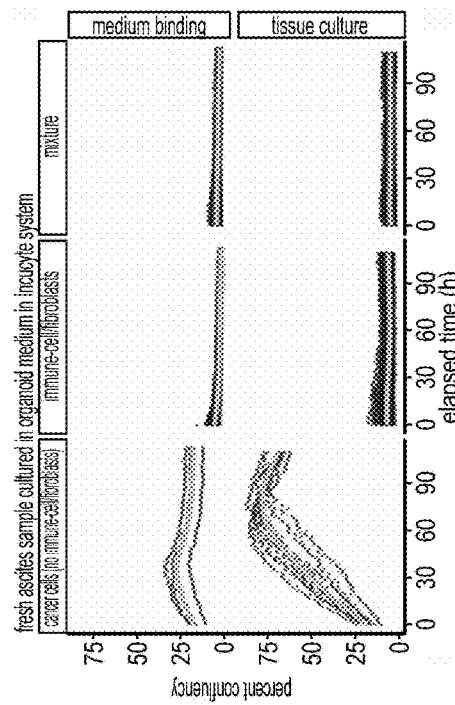
FIG. 2A
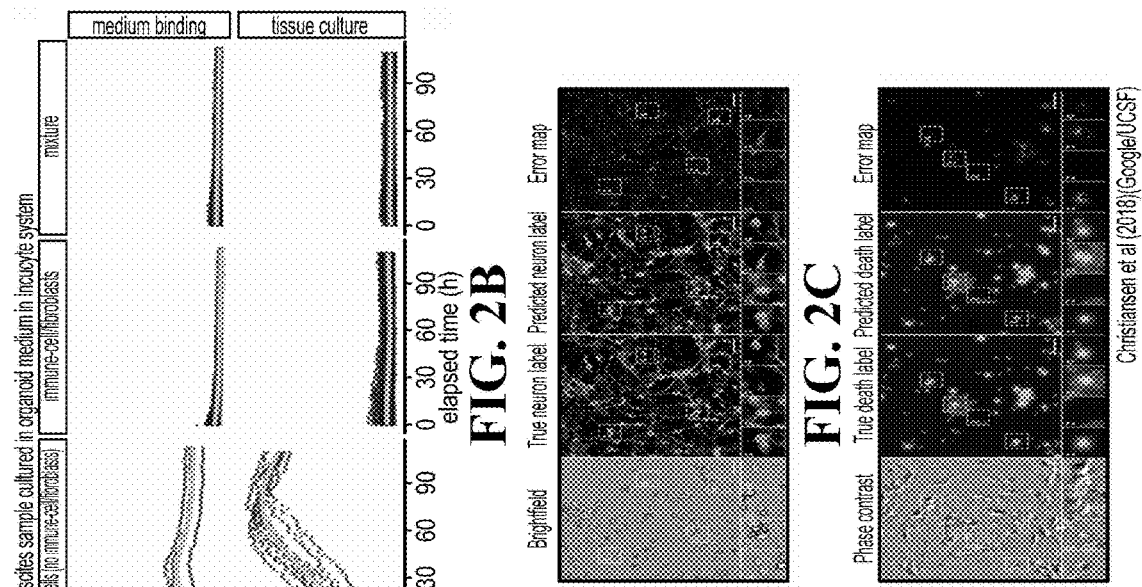
FIG. 2B
FIG. 2C
FIG. 2D ed on Nov. 23, 2020) is herein incorporated by reference in its entirety.

SEQUENCE LISTING

```
<160> NUMBER OF SEQ ID NOS: 19

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 10
<212> TYPE: PRT
<213> ORGANISM: Simian virus 40

<400> SEQUENCE: 2

Pro Lys Lys Lys Arg Lys Val Glu Ala Ser
1               5                   10

<210> SEQ ID NO 3
<211> LENGTH: 16
```

```
<212> TYPE: PRT
<213> ORGANISM: Artificial Sequence
<220> FEATURE:
<223> OTHER INFORMATION: Synthetic nucleoplasmin bipartite NLS

<400> SEQUENCE: 3

Lys Arg Pro Ala Ala Thr Lys Lys Ala Gly Gln Ala Lys Lys Lys Lys
1               5                   10                  15

<210> SEQ ID NO 4
<211> LENGTH: 9
<212> TYPE: PRT
<213> ORGANISM: Homo sapiens

<400> SEQUENCE: 4

Pro Ala Ala Lys Arg Val Lys Leu Asp
1               5

<210> SEQ ID NO 5
<211> LENGTH: 11
<212> TYPE: PRT
<213> ORGANISM: Homo sapiens

<400> SEQUENCE: 5

Arg Gln Arg Arg Asn Glu Leu Lys Arg Ser Pro
1               5                   10

<210> SEQ ID NO 6
<211> LENGTH: 38
<212> TYPE: PRT
<213> ORGANISM: Homo sapiens

<400> SEQUENCE: 6

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
                35

<210> SEQ ID NO 7
<211> LENGTH: 42
<212> TYPE: PRT
<213> ORGANISM: Homo sapiens

<400> SEQUENCE: 7

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
                35                  40

<210> SEQ ID NO 8
<211> LENGTH: 8
<212> TYPE: PRT
<213> ORGANISM: Homo sapiens

<400> SEQUENCE: 8

Val Ser Arg Lys Arg Pro Arg Pro
1               5

<210> SEQ ID NO 9
```

```
<211> LENGTH: 8
<212> TYPE: PRT
<213> ORGANISM: Homo sapiens

<400> SEQUENCE: 9

Pro Pro Lys Lys Ala Arg Glu Asp
1               5

<210> SEQ ID NO 10
<211> LENGTH: 8
<212> TYPE: PRT
<213> ORGANISM: Homo sapiens

<400> SEQUENCE: 10

Pro Gln Pro Lys Lys Lys Pro Leu
1               5

<210> SEQ ID NO 11
<211> LENGTH: 12
<212> TYPE: PRT
<213> ORGANISM: Mus sp.

<400> SEQUENCE: 11

Ser Ala Leu Ile Lys Lys Lys Lys Lys Met Ala Pro
1               5                   10

<210> SEQ ID NO 12
<211> LENGTH: 5
<212> TYPE: PRT
<213> ORGANISM: Influenza virus

<400> SEQUENCE: 12

Asp Arg Leu Arg Arg
1               5

<210> SEQ ID NO 13
<211> LENGTH: 7
<212> TYPE: PRT
<213> ORGANISM: Influenza virus

<400> SEQUENCE: 13

Pro Lys Gln Lys Lys Arg Lys
1               5

<210> SEQ ID NO 14
<211> LENGTH: 10
<212> TYPE: PRT
<213> ORGANISM: Hepatitis D virus

<400> SEQUENCE: 14

Arg Lys Leu Lys Lys Lys Ile Lys Lys Leu
1               5                   10

<210> SEQ ID NO 15
<211> LENGTH: 10
<212> TYPE: PRT
<213> ORGANISM: Mus sp.

<400> SEQUENCE: 15

Arg Glu Lys Lys Lys Phe Leu Lys Arg Arg
1               5                   10

<210> SEQ ID NO 16
<211> LENGTH: 20
<212> TYPE: PRT
```

```
<213> ORGANISM: Homo sapiens

<400> SEQUENCE: 16

Lys Arg Lys Gly Asp Glu Val Asp Gly Val Asp Glu Val Ala Lys Lys
1               5                   10                  15

Lys Ser Lys Lys
            20

<210> SEQ ID NO 17
<211> LENGTH: 17
<212> TYPE: PRT
<213> ORGANISM: Homo sapiens

<400> SEQUENCE: 17

Arg Lys Cys Leu Gln Ala Gly Met Asn Leu Glu Ala Arg Lys Thr Lys
1               5                   10                  15

Lys

<210> SEQ ID NO 18
<211> LENGTH: 288
<212> TYPE: PRT
<213> ORGANISM: Artificial Sequence
<220> FEATURE:
<223> OTHER INFORMATION: Synthetic N-terminal capping region

<400> SEQUENCE: 18

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
```

```
                    245                 250                 255
Thr Gly Gln Leu Leu Lys Ile Ala Lys Arg Gly Val Thr Ala Val
            260                 265                 270

Glu Ala Val His Ala Trp Arg Asn Ala Leu Thr Gly Ala Pro Leu Asn
            275                 280                 285

<210> SEQ ID NO 19
<211> LENGTH: 183
<212> TYPE: PRT
<213> ORGANISM: Artificial Sequence
<220> FEATURE:
<223> OTHER INFORMATION: Synthetic C-terminal capping region

<400> SEQUENCE: 19

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
            35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
            115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180
```

LIVING BIOSENSORS

CROSS-REFERENCE TO RELATED APPLICATIONS

This application claims the benefit of U.S. Provisional Application No. 62/944,880, filed Dec. 6, 2019. The entire contents of the above-identified application are hereby fully incorporated herein by reference.

REFERENCE TO AN ELECTRONIC SEQUENCE LISTING

The contents of the electronic sequence listing ("BROD-4680US_ST25.txt"; Size is 7904 bytes, and it was created on Nov. 23, 2020) is herein incorporated by reference in its entirety.

TECHNICAL FIELD

The subject matter disclosed herein is generally directed to ex-vivo cell-based living biosensor models, methods and uses thereof.

BACKGROUND

The ability to infer dependencies given the molecular features of a patient's tumor is central to cancer precision medicine. Ongoing clinical and laboratory efforts aim to develop reference data to improve the accuracy of such inferences, in part by correlating molecular features of patient tumors with therapeutic outcomes. While laboratory efforts can be systematic and unbiased, they are bounded both by the subset of human tumors that can be propagated as long-term cell models and by the inability to retain the cellular diversity of real tumors in such models. Making living, heterogeneous tissues compatible with ex vivo functional genomics, as well as imaging that does not destroy the tissue would aid in efforts towards cancer precision medicine.

Citation or identification of any document in this application is not an admission that such a document is available as prior art to the present invention.

SUMMARY

In certain example embodiments, a method of identifying cell types and/or cell phenotypes in an ex vivo sample is provided, comprising imaging the sample; perturbing cells in the sample; and identifying cell types and/or cell phenotypes of the sample at a single cell resolution over a period of time. In certain embodiments, the imaging comprises fluorescent microscopy or transmitted-light microscopy. In an aspect, the imaging of the sample is label-free imaging.

Identifying the cell types and/or cell phenotypes can comprise utilizing morphologic classifiers. In embodiments, the morphologic classifiers are built using convolutional neural networks.

Identifying cell phenotypes may comprise characterizing perturbation-induced cellular death and non-perturbation induced cellular death. The perturbing may comprise exposing one or more cells to one or more drugs, which, in one aspect may be a cytotoxic agent, targeted agent or immunomodulating agent. In some embodiments, the methods can further comprise classifying drug sensitive and drug insensitive cells in the sample. In an aspect, perturbing comprises perturbing one or more target genes in the cells of the sample so as to identify cell phenotypes including characterizing perturbation-induced cellular death and non-perturbation induced cellular death.

Perturbing one or more target genes can comprise gene knock-down, gene knock-out, gene activation, gene insertion, or regulatory element deletion. In an aspect, perturbing one or more genes in the cells of the sample comprises performing RNAi-based perturbation, or performing CRISPR-Cas based perturbation. The perturbing can comprise performing single or combinatorial CRISPR-Cas-based perturbation; the CRISPR-Cas based perturbation can comprise targeted base editing.

Methods can comprise continuous imaging of the samples; in an aspect, continuous imaging is performed over 24 hour time period, over a 48 hour time period, over a 72 hour time period, over a 96 hour time period, over a 120 hour time period, or over a 144 hour time period. Imaging can be performed at one or more timepoints.

The sample may be aseptically collected from a subject. In an aspect, the sample is fresh or the sample is cryopreserved. The sample may be from a tumor, which may be a solid tumor, a liquid tumor, a primary tumor sample or a metastatic tumor sample. The sample may be ascites fluid. Methods may further comprise the step of propagating the cells of the sample. The sample may comprise a cultured organoid, a cultured cell line, or a cultured spheroid culture.

Methods may comprise the step of distributing the sample into one or more individual discrete volumes, in an aspect, at least one discrete volume is not perturbed with active agent.

A method of monitoring drug sensitivity in a subject in need thereof, is provided, comprising detecting the drug sensitivity of the cells according to any one of the methods disclosed herein in a sample obtained from the subject. Methods may comprise detecting drug sensitivity in two or more samples obtained from the subject for at least two time points. In an aspect, at least one sample is obtained before treatment, or at least one sample is obtained after treatment. Methods may comprise comparing the drug sensitivity of the two samples to inform the course of treatment. Methods may comprise monitoring of each sample occurs over a time window of less than about 10 days, less than about 5 days, or less than about 72 hours after perturbing the cells.

A method of generating a living biosensor cell model is provided in certain embodiments, comprising distributing a sample of cells into one or more individual discrete volumes; perturbing one or more of the individual discrete volumes with one or more agents; and identifying cell types and/or cell phenotypes of the sample at a single cell resolution over a period of time. As described herein, identifying the cell types and/or cell phenotypes can comprise utilizing morphologic classifiers, wherein the morphologic classifiers can be built using a convolutional neural network. Generating a living biosensor cell model can further comprise utilizing methods identifying cell phenotypes which can comprise characterizing perturbation-induced cellular death and non-perturbation induced cellular death. Agents used with the methods may comprise one or more drugs, wherein the one or more drugs is a cytotoxic agent, targeted agent or immunomodulating agent.

Perturbing may comprise perturbing one or more target genes in the cells of the sample, which may comprise gene knock-down, gene knock-out, gene activation, gene insertion, or regulatory element deletion. The agent may be miRNA, shRNA, or siRNA.

Generation of the living biosensor models may comprise perturbing one or more genes by performing CRISPR-Cas based perturbation, which, in an aspect, may be single or combinatorial CRISPR-Cas-based perturbation, or may comprise performing targeted base editing.

As disclosed herein, the sample may be collected aseptically from the subject. The sample for generating the living biosensors may be fresh or cryopreserved. The sample may be from a tumor, a solid tumor, a hematological malignancy, a primary tumor sample or a metastatic tumor sample. The sample may be ascites fluid.

In certain embodiments, the living biosensor cell model is designed to live between about 3 days and about 1 month. An ex vivo cell-based system derived from any of the methods as disclosed herein is also provided. The cell-based system may comprise one or more cell types, wherein one or more cell types comprises a tumor cell. Use of the cell-based systems may comprise identifying a therapeutic agent or determining the efficacy of a therapeutic agent. Use of the cell-based system may comprise selecting one or more therapeutic agents for treatment of a subject in need thereof, or for screening agents having antitumor activity.

A direct to subject kit for collecting a fresh aseptic sample is provided, comprising a container configured to collect the sample from a subject in an aseptic manner, instructions for collection and shipment of the sample, and a temperature control mechanism that maintains the integrity of the sample during shipment. The kit may comprise a container that is adapted to connect to the subject drain.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 2A-2D—Pilot project overview. FIG. 2A Schematic of planned sample flow after receipt at the Broad; FIG. 2B Using real-time imaging to optimize culture conditions and timescale for CD45-gastroesophageal ascites cells over first 24-96 hours of ex vivo propagation (Incucyte example); FIG. 2C, 2D imaging using convolutional networks to classify cell type (FIG. 2C) and cell death (FIG. 2D) from transmitted light images, without the need for fluorescence-based endpoint staining (Chistiansen et al., 2018, Ounkuomol et al, 2018).

Figure 1:
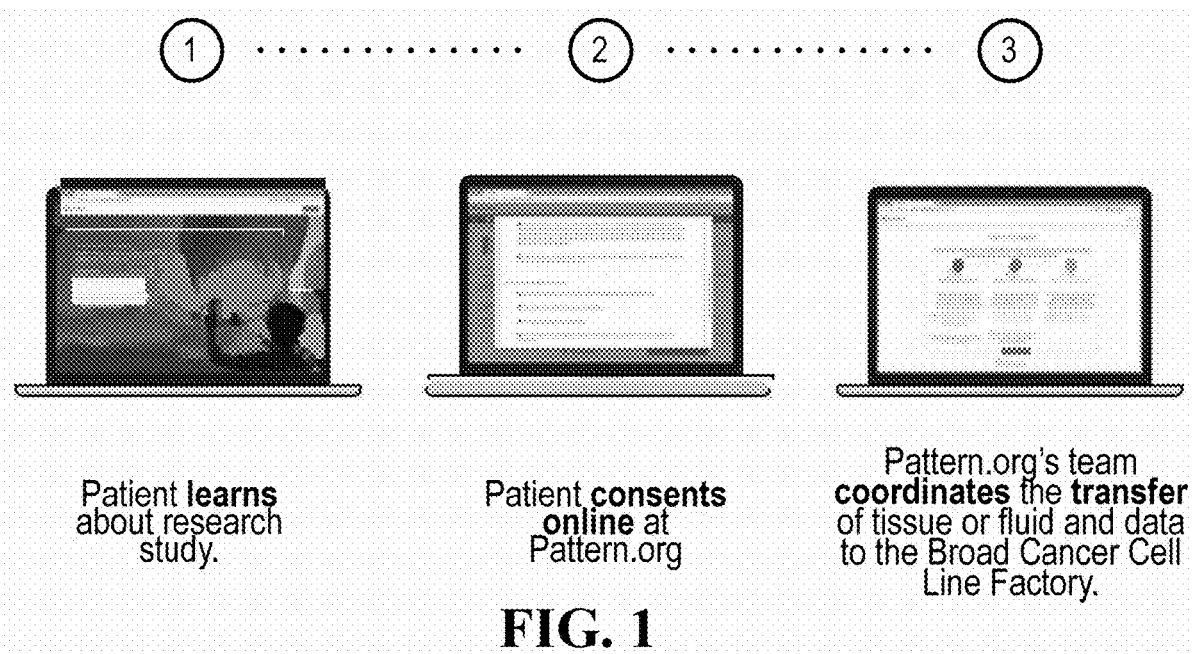
FIG. 1—Patient-partnered pipeline for fresh tissue acquisition. Workflow from patients to the Broad Institute, with 88 institutions represented by 135 consents from patients with rare tumors, producing 77 fresh tissue samples to the Broad Institute for organoid/cell line propagation.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein generally applicable framework that utilizes label free imaging to identify cell types and/or cell phenotypes in an ex vivo tumor sample. The systems and methods developed allow for rapid testing of perturbations in tumor samples, allowing the system to work as a living biosensor for detection of drug susceptibilities and other differentiation in a heterogeneous cell sample.

In one aspect, the present invention provides for a method of generating an ex vivo cell-based system from a tumor sample. The tumor sample can be collected during surgery or by a clinician, or can be collected by a patient in an aseptic manner at home.

One or more cell types or one or more cell states in an initial cell-based system can be imaged; the one or more cell types in the sample can be exposed to one or more perturbations, and imaged—either continuously or at various time points, which allows identification differences in one or more cell types and/or cell states between the initial cell-based system and the perturbed system.

Systems for Identification of Cell Types and Phenotypes

Systems for identification of cell types and cell phenotypes, such as drug susceptibility, for sample are provided herein. Such systems operate as living biosensors, distinguishing cancer cells, from immune cells and other cell types present in sample mixtures and describing their viability. Response to perturbations can also be interrogated using the systems described herein. Exemplary uses of the systems may include for selection of one or more therapeutic agents for treatment of a subject in need thereof, in methods for screening agents having antitumor activity, for identification of a therapeutic agent or to determine the efficacy of a therapeutic agent, as described elsewhere herein.

In an aspect, the present invention provides for an ex vivo cell-based system derived from any embodiment herein, wherein the single cell type or subtype or combination of cell types and/or subtypes comprises a tumor cell. An "ex vivo cell-based system" may comprise single cells of a particular type, sub-type or state, or a combination of cells of the same or differing type, sub-type, or state. The ex vivo cell-based system may be a model for screening perturbations to better understand the underlying biology or to identify putative targets for treating a disease, or for screening putative therapeutics.

In another aspect, the present invention provides for an ex vivo cell-based system derived from any embodiment herein, wherein the single cell type or subtype or combination of cell types and/or subtypes comprises a tumor cell. The sample may comprise a tumor microenvironment cell, for example a tumor infiltrating lymphocyte (TIL). The tumor microenvironment (TME) is the cellular environment in which the tumor exists, including surrounding blood vessels, immune cells, cancer associated fibroblasts (CAFs), bone marrow-derived inflammatory cells, lymphocytes, signaling molecules and the extracellular matrix (ECM). Tumor infiltrating lymphocytes (TILs) are lymphocytes that penetrate a tumor.

The systems can be designed to live less than about 6 weeks, between about 3 days and about 1 month, or about 3, 4, 5, 6, 7, 8, 9, 10, 11, 12, 13, 14, 15, 16, 17, 18, 19, 20, 21, 22, 23, 24, 25, 26, 27, 28, 29, 30 or 31 days.

The single cell type or subtype or combination of cell types and/or subtypes may be perturbed by one or more drugs, which may be one or more immunotherapies, targeted agents, or cytotoxic agents. The immunotherapy may be checkpoint blockade therapy (CBT). The sample may be derived from a subject with cancer, with a cancer recurrence, with advanced cancer. The sample may be from a subject with a port or drain that allows patient to collect fluid from the port or drain, for example, after a tumor resection surgery, or for drainage of ascites fluid.

Sample

In certain embodiments, the initial cell-based system comprises a single cell type or sub-type, a combination of cell types and/or subtypes, or an organoid. Embodiments may comprise a solid tumor sample, a primary tumor sample, or metastatic tumor sample. In embodiments, the sample is an epithelial tumor sample. Particular sample types may also include from a hematological malignancy or ascites fluid.

The sample may be used for an ex vivo cell-based system derived from any embodiment herein. In embodiments, the system can be derived from a sample that comprises ex vivo propagation. In embodiments, the system comprises a cultured two dimensional or three-dimensional culture. For example, the culture may comprise a cell line, spheroid or organoid model. As used herein, the term organoid or epithelial organoid refers to a cell cluster or aggregate that resembles an organ, or part of an organ, and possesses cell types relevant to that particular organ. The sample can be a spheroid culture, a three-dimensional multicellular aggregate. Accordingly, in embodiments, the methods of using the living biosensor systems comprise propagating the cells of the sample.

The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v $CO_2$ and >95% humidity.

The tumor sample may be obtained from any mammal. Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

In certain embodiments, a sample is obtained from a subject. As used herein, a "sample", "tissue sample", or "biological sample" may contain whole cells and/or live cells and/or cell debris. The sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, ascites fluid, vomit and mixtures of one or more thereof. Biological samples include cell cultures, bodily fluids, cell cultures from bodily fluids. Bodily fluids may be obtained from a mammal organism, for example by puncture, or other collecting or sampling procedures. In certain embodiments, the sample is collected from a subject drain, which may include collection into a container adapted to connect to a subject drain.

The methods disclosed herein may be used to develop an ex vivo cell-based system de novo from a source starting material. Source starting materials may include cultured cell lines, but preferably include sample cells or tissues isolated directly from an in vivo source, including explants and biopsies. In embodiments, the sample can comprise profiling of a first sample to a second sample. Such samples may comprise, for example, a first biopsy sample to a second biopsy sample. In embodiments, a first sample can be, for example a healthy tissue sample, primary tumor sample or ascites fluid sample. A second sample may comprise a putative metastatic biopsy sample, later captured tissue sample or biopsy, including a tissue or cell sample that is collected subsequent to a treatment in a subject, e.g., immunotherapy, chemotherapy.

Collected samples utilized may be fresh samples or may be cryopreserved. Cells can be obtained from a solid tissue sample by dissociating the tissue sample into a cell suspension from which specific cell populations can be selected. Suitable methods of may include, but are not limited to, any one or more of mechanically dissociating (e.g., mincing) the tumor, enzymatically dissociating (e.g., digesting) the tumor, and aspiration (e.g., as with a needle).

Cell Types and Subtypes

In certain embodiments, the single cell population may comprise a single cell type or subtype or combination of cell types and/or subtypes. Exemplary cell types and/or subtypes include an immune cell, intestinal cell, liver cell, kidney cell, lung cell, brain cell, epithelial cell, endoderm cell, neuron, ectoderm cell, islet cell, acinar cell, oocyte, sperm, hematopoietic cell, hepatocyte, skin/keratinocyte, melanocyte, bone/osteocyte, hair/dermal papilla cell, cartilage/chondrocyte, fat cell/adipocyte, skeletal muscular cell, endothelium cell, cardiac muscle/cardiomyocyte, trophoblast, tumor cell, or tumor microenvironment (TME) cell. Cell types and/or subtypes can be defined in whole or in part on the basis of imaging conducted alone or in combination with further morphologic classifiers, perturbations and/or other features. The features, such as, for example, one or more of: cell type, granularity, drug susceptibility, drug sensitivity or insensitivity, cell phase, apoptosis, characterization of stress-related cell death across samples, or for a particular cell type in a sample or sample source, are extracted from the images. Exemplary cell types include immune cells (CD45) and apoptotic cells. In certain embodiments, the methods and systems include identification of high-level cell types (e.g. malignant vs. immune vs. stromal vs. other). In certain embodiments, the methods and systems cell subtypes, subcellular composition, cell states, and/or phenotypes, such as apoptosis are utilized. Signatures as discussed herein can be specific to a particular pathological context, cell type and/or cell subtype. Not being bound by a theory, a combination of cell subtypes having a particular signature may indicate an outcome.

Cancer

In certain example embodiments, the systems and methods may be used to identify the pharmaceutical compositions and therapies that may be used to treat various forms of cancer. Samples derived from subjects having, or suspected of having cancer are contemplated for use with the currently disclosed systems and methods. Cell cancer types and features, including responsiveness to perturbations, cell surface markers and Examples of cancer include but are not limited to carcinoma, lymphoma, blastoma, sarcoma, and leukemia or lymphoid malignancies. More particular examples of such cancers and associated cell types and/or subtypes include without limitation: squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioma, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as CNS cancer, melanoma, head and neck cancer, bone cancer, bone marrow cancer, duodenum cancer, esophageal cancer, thyroid cancer, or hematological cancer.

Other non-limiting examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumours, Breast Cancer, Cancer of the Renal Pelvis and Urethra, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Glioblastoma, Childhood Cerebellar Astrocytoma, Childhood Cerebral Astrocytoma, Childhood Extracranial Germ Cell Tumours, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumours, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumours, Exocrine Pancreatic Cancer, Extracranial Germ Cell Tumour, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumour, Gastrointestinal Tumours, Germ Cell Tumours, Gestational Trophoblastic Tumour, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumour, Ovarian Low Malignant Potential Tumour, Pancreatic Cancer, Paraproteinemias, Purpura, Parathyroid Cancer, Penile Cancer, Pheochromocytoma, Pituitary Tumour, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Urethra Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumours, T-Cell Lymphoma, Testicular Cancer, Thymoma, Thyroid Cancer, Transitional Cell Cancer of the Renal Pelvis and Urethra, Transitional Renal Pelvis and Urethra Cancer, Trophoblastic Tumours, Urethra and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, or Wilms' Tumor.

Methods of Identifying Cell Types and/or Cell Phenotypes

The living biosensor systems can be utilized for identifying cell types and/or cell phenotypes in the ex vivo sample. The methods of identifying cell types and/or cell phenotypes can comprise the steps of imaging the sample; perturbing cells in the sample; and identifying cell types and/or cell phenotypes of the sample at a single cell resolution over a period of time. Imaging the sample may comprise fluorescent microscopy, transmitted-light microscopy, which may in an aspect comprise label-free imaging.

Imaging the Sample

Label-free imaging may be used for imaging of the sample. Label-free imaging advantageously allows imaging of samples without damage to the cells in the sample. In embodiments, imaging is performed without staining.

In one aspect, the label free imaging can be used with a modified approach as described in Christiansen et al., In Silico Labeling: Predicting Fluorescent Labels in Unlabeled Images Cell. April 19; 173(3):792-803.e19. doi: 10.1016/j.cell.2018.03.040. Epub 2018 Apr. 12.

Imaging can be utilized continuously or at particular time points, for example, prior to perturbing and at one or more time points subsequent to perturbing. Continuous imaging may be performed over a 24 hour time period, a 48 hour time period, a 72 hour time period, a 96 hour time period, a 120 hour time period, a 144 hour time period, or more. Imaging may also be performed at one or more timepoints, for example one or more timepoints prior to perturbing and subsequent to perturbing.

In an aspect, the imaging is transmitted-light microscopy, for example, bright field imaging or phase contrast. The image can be collected from a sample, such as a cell, where contrast in the sample is caused by absorbance of some of the transmitted light in dense areas of the sample. The typical appearance of a brightfield image is a dark sample on a bright background.

In one aspect, the imaging is collected in real-time. Imaging features extracted from the brightfield images alone can be sufficient to classify the cells for morphologic features, phenotypes or other cell classifiers.

Imaging in this manner allows the cells to be labeled without the use of additional stains, which may have confounding effects on the cells, with samples used in imaging allowing for further analysis of the same cells over time as the cells are not otherwise altered by use of stains.

Images of a cell or a set of cells can be acquired and/or received. These images include features which can be used to define or classify the cell shown in the image. The features, such as, for example, one or more of: cell type, granularity, drug susceptibility, drug sensitivity or insensitivity, cell phase, apoptosis, characterization of stress-related cell death across samples, or for a particular cell type in a sample are extracted from the images. Characterizing cell death may include distinguishing between perturbation-induced cellular death and non-perturbation-induced cellular death. Cell survival can be identified based on predictions of images of live cells treated with propidium iodide, which preferentially labels dead cells. Apoptosis can be characterized in some cells by comparing the size and shape of nuclei. Extraction of data from the image can be based on morphologic classifiers that distinguish cancer from immune cells, and from other cell types present in a sample and further describing the cellular viability.

Using the extracted features, a cell shown in the one or more images is classified using a classifier that has been trained on a control sample to recognize and classify the cells in the images based on the features and values derived therefrom, i.e. morphologic classifiers.

Morphologic Classifiers

Morphologic classifiers can be built using convolutional neural networks, deep learning algorithms that take an input image, assign importance, e.g. learnable weights/biases to the objects in the image to differentiate aspects or objects in the image from the other. For example, a pre-trained in silico network, adapted from the approach described in Christiansen et al., which is a deep learning system, can be used to predict fluorescent labels from transmitted light images with high correlation between location and fluorescence intensity of actual and predicted pixels. In one exemplary embodiment, the pre-trained network is trained to predict fluorescent dye channels based on a set of samples that are fluorescently labeled. A three-dimensional set of a plurality of label-free images is then collected, and an algorithm is applied to the set, returning a set of two-dimensional images, each image representing a fluorescent dye channel the network was initially trained to predict.

In an embodiment, the network is trained to predict fluorescent labels for fluorescent markers. In embodiments, the network is trained for CD45 immunofluorescence, one or more fluorescent markers or both. In an embodiment, one or more of the fluorescent markers comprise a caspase reactive fluorescent marker, for example CellEvent. The network can be trained on a set of images comprising ground-truth fluorescent markers for immune cells (CD45) and apoptotic cells. The network can be trained to classify high level cell types (e.g. malignant vs. immune vs. stromal vs. other), cell subtypes, subcellular composition, cell states, and/or phenotypes, such as apoptosis.

Morphologic features include changes as a result of cell death due to drugs, without drugs and supplemental or drug-class specific morphologic changes can also be determined according to the current methods. Accordingly, drug-sensitive and drug insensitive cells within heterogeneous mixtures of a cell sample can be utilized. The network can be trained to extract morphologic features of the cells. In the case of cell classification, the algorithm identifies patterns in the input images and trains a model based on labels which were assigned to the cells in the images. Features can include shape and phase value of the cell, including footprint area of a cell, convex area of a cell, solidity roundness, indentation of cell boundary, eccentricity, average phase value in the cell region, etc. Nuclei can be imaged, for example, nuclei staining by DAPI and/or Hoescht staining can be used to train the neural network.

To confirm predictions, results can be compared against sc-RNAseq data, serial biological replicate samples from the same subject taken several weeks apart, and/or clinical response annotations from a retrospective collection of samples.

In one aspect, the method comprises classifying cells based directly on the images, i.e., without extracting features. In one aspect, the method comprises a computer-implemented method for the label-free classification of cells using image cytometry, comprising: receiving, by one or more computing devices, one or more images of a cell obtained from an image cytometer; classifying, by the one or more computing devices, the cell based on the images using machine learning methods; outputting by the one or more computing devices, the class label of the cell.

In some embodiments between about 2 and about 75000 features are extracted from the images, such as 5 or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more 95 or more, 100 or more, 200 or more, 300 or more, 400 or more, 500 or more, 1000 or more, 2000 or more, 3000 or more, 4000 or more, 5000 or more, or 10000 or more. In embodiments, the morphologic classifiers can be built from a fluorescent label-predicting convolutional neural network, where networks can contain millions of trainable parameters.

Particular screening applications of this invention relate to the testing of pharmaceutical compounds in drug research. The reader is referred generally to the standard textbook In vitro Methods in Pharmaceutical Research, Academic Press, 1997, and U.S. Pat. No. 5,030,015. In certain aspects of this invention, the culture of the invention is used to test cells for standard drug screening and toxicity assays. Assessment of the activity of candidate pharmaceutical compounds generally involves contacting the candidate compound to an individual discrete volume of the sample, determining any change in the morphology, marker phenotype, or metabolic activity of the cells that is attributable to the candidate compound (compared with untreated cells or cells treated with an inert compound, such as vehicle) by label free imaging methods as disclosed herein, and then correlating the effect of the candidate compound with the observed change. The screening may be done because the candidate compound is designed to have a pharmacological effect on the ex vivo sample, or because a candidate compound may have unintended side effects on the ex vivo sample. Alternatively, libraries can be screened without any predetermined expectations in hopes of identifying compounds with desired effects. Cytotoxicity can be determined in the first instance by the effect on cell viability and morphology as determined by the imaging methods provided herein.

Additional further uses of the systems of the invention include, but are not limited to, its use in research e.g., to elucidate mechanisms leading to the identification of novel targets for therapies, and to generate systems such as organoids and cell lines for disease modeling, including the generation of new therapies customized to different genotypes. Such customization can reduce adverse drug effects and help identify therapies appropriate to the patient's genotype.

Individual Discrete Volumes

A sample can be distributed into one or more individual discrete volumes, which can be utilized to generate a plurality of perturbations of a sample each in a discrete space. An "individual discrete volume" is a discrete volume or discrete space, such as a container, receptacle, or other defined volume or space that can be defined by properties that prevent and/or inhibit migration of nucleic acids, CRISPR detection systems, and reagents necessary to carry out the methods disclosed herein, for example a volume or space defined by physical properties such as walls, for example the walls of a well, tube, or a surface of a droplet, which may be impermeable or semipermeable, or as defined by other means such as chemical, diffusion rate limited, electro-magnetic, or light illumination, or any combination thereof. In particularly preferred embodiments, the individual discrete volumes are droplets. By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electro-magnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the use of non-walled, or semipermeable is that some reagents, such as buffers, chemical activators, or other agents maybe passed in or through the discrete volume, while other material, such as target molecules, maybe maintained in the discrete volume or space. As explained herein, a droplet system allows for the separation of compounds until initiation of a reaction is desired. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain example embodiments, the individual discrete volumes are droplets.

In particular embodiments, subsequent to distributing the sample into one or more discrete volumes, the step of introducing one or more perturbations to the individual discrete volumes is performed. In embodiments, at least one discrete volume is not perturbed with an active agent. In embodiments, the at least one discrete volume that is not perturbed with active agent may be termed a control.

The term "control" refers to any reference standard suitable to provide a comparison to the test sample. In one embodiment, the control comprises obtaining a "control sample" from which cell types/phenotypes are detected and compared to cell types/phenotypes from the test sample. Such a control sample may comprise any suitable sample, including but not limited to a sample from a control patient (can be stored sample or previous sample measurement) with a known outcome; normal tissue, fluid, or cells isolated from a subject, such as a normal patient or the patient having a condition of interest, samples that are not subject to perturbing with an active agent, e.g. exposed to inert treatment or substance, placebo, inactive solvents or carrier fluids.

Perturbing the Cells

In certain embodiments, perturbing the initial cell-based system comprises delivering one or more modulating agents that modify expression of one or more cell types or states in the initial cell-based system, delivering an additional cell type or sub-type to the initial cell-based system, or depleting an existing cell type or sub-type from the initial cell-based system. Perturbing may comprise perturbing one or more target genes in the cells in the sample.

The one or more modulating agents may comprise one or more drugs, cytokines, growth factors, hormones, transcription factors, metabolites or small molecules. The one or more modulating agents may be a genetic modifying agent or an epigenetic modifying agent. The genetic modifying agent may comprise a CRISPR system, a zinc finger nuclease system, a TALEN, or a meganuclease. The epigenetic modifying agent may comprise a DNA methylation inhibitor, HDAC inhibitor, histone acetylation inhibitor, histone methylation inhibitor or histone demethylase inhibitor. Perturbing may comprise gene knock-down, gene knock-out, gene activation, gene insertion, base editing, or regulatory element deletion.

In certain embodiments, modulating the ex vivo cell-based system comprises delivering one or more modulating agents that modify expression of one or more cell types or states in the ex vivo cell-based system, delivering an additional cell type or sub-type to the ex vivo cell-based system, or depleting an existing cell type or sub-type from the ex vivo cell-based system.

The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of a cell or cell population may be modulated without substantially altering other (unintended, undesired) phenotypic aspect(s).

Non-limiting examples of hormones include growth hormone (GH), adrenocorticotropic hormone (ACTH), dehydroepiandrosterone (DHEA), cortisol, epinephrine, thyroid hormone, estrogen, progesterone, testosterone, or combinations thereof.

Non-limiting examples of cytokines include lymphokines (e.g., interferon-γ, IL-2, IL-3, IL-4, IL-6, granulocyte-macrophage colony-stimulating factor (GM-CSF), interferon-γ, leukocyte migration inhibitory factors (T-LIF, B-LIF), lymphotoxin-alpha, macrophage-activating factor (MAF), macrophage migration-inhibitory factor (MIF), neuroleukin, immunologic suppressor factors, transfer factors, or combinations thereof), monokines (e.g., IL-1, TNF-alpha, interferon-α, interferon-β, colony stimulating factors, e.g., CSF2, CSF3, macrophage CSF or GM-CSF, or combinations thereof), chemokines (e.g., beta-thromboglobulin, C chemokines, CC chemokines, CXC chemokines, CX3C chemokines, macrophage inflammatory protein (MIP), or combinations thereof), interleukins (e.g., IL-1, IL-2, IL-3, IL-4, IL-5, IL-6, IL-7, IL-8, IL-9, IL-10, IL-11, IL-12, IL-13, IL-14, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, or combinations thereof), and several related signaling molecules, such as tumour necrosis factor (TNF) and interferons (e.g., interferon-α, interferon-β, interferon-γ, interferon-λ, or combinations thereof).

Non-limiting examples of growth factors include those of fibroblast growth factor (FGF) family, bone morphogenic protein (BMP) family, platelet derived growth factor (PDGF) family, transforming growth factor beta (TGFbeta) family, nerve growth factor (NGF) family, epidermal growth factor (EGF) family, insulin related growth factor (IGF) family, hepatocyte growth factor (HGF) family, hematopoietic growth factors (HeGFs), platelet-derived endothelial cell growth factor (PD-ECGF), angiopoietin, vascular endothelial growth factor (VEGF) family, glucocorticoids, or combinations thereof.

Non-limiting examples of mitogens include phytohaemagglutinin (PHA), concanavalin A (conA), lipopolysaccharide (LPS), pokeweed mitogen (PWM), phorbol ester such as phorbol myristate acetate (PMA) with or without ionomycin, or combinations thereof.

Non-limiting examples of cell surface receptors the ligands of which may act as immunomodulants include Toll-like receptors (TLRs) (e.g., TLR1, TLR2, TLR3, TLR4, TLR5, TLR6, TLR7, TLR8, TLR9, TLR10, TLR11, TLR12 or TLR13), CD80, CD86, CD279 (PD1), CD274 (PDL1), CD40, CCR7, or C-type lectin receptors.

In certain embodiments, differentiation promoting agents may be used to obtain particular types of target cells. Differentiation promoting agents include anticoagulants, chelating agents, and antibiotics. Examples of such agents may be one or more of the following: vitamins and minerals or derivatives thereof, such as A (retinol), B3, C (ascorbate), ascorbate 2-phosphate, D such as $D_2$ or $D_3$, K, retinoic acid, nicotinamide, zinc or zinc compound, and calcium or calcium compounds; natural or synthetic hormones such as hydrocortisone, and dexamethasone; amino acids or derivatives thereof, such as L-glutamine (L-glu), ethylene glycol tetracetic acid (EGTA), proline, and non-essential amino acids (NEAA); compounds or derivatives thereof, such as β-mercaptoethanol, dibutyl cyclic adenosine monophosphate (db-cAMP), monothioglycerol (MTG), putrescine, dimethyl sulfoxide (DMSO), hypoxanthine, adenine, forskolin, cilostamide, and 3-isobutyl-1-methylxanthine; nucleosides and analogues thereof, such as 5-azacytidine; acids or salts thereof, such as ascorbic acid, pyruvate, okadic acid, linoleic acid, ethylenediaminetetraacetic acid (EDTA), anticoagulant citrate dextrose formula A (ACDA), disodium EDTA, sodium butyrate, and glycerophosphate; antibiotics or drugs, such as G418, gentamicin, Pentoxifylline (1-(5-oxohexyl)-3,7-dimethylxanthine), and indomethacin; and proteins such as tissue plasminogen activator (TPA).

Genetic Modifying Agents

In certain embodiments, the one or more modulating agents may be a genetic modifying agent or an epigenetic modifying agent. The genetic modifying agent may comprise a CRISPR system, a zinc finger nuclease system, a TALEN, or a meganuclease. The epigenetic modifying agent may comprise a DNA methylation inhibitor, HDAC inhibitor, histone acetylation inhibitor, histone methylation inhibitor or histone demethylase inhibitor.

In some embodiments, the adenosine deaminase comprises a mutation at glutamic acid$^{1008}$ of the hADAR1-D amino acid sequence, or a corresponding position in a homologous ADAR protein. In some embodiments, the glutamic acid residue at position 1008 is replaced by a polar amino acid residue having a relatively large side chain. In some embodiments, the glutamic acid residue at position 1008 is replaced by a glutamine residue (E1008Q). In some embodiments, the glutamic acid residue at position 1008 is replaced by a histidine residue (E1008H). In some embodiments, the glutamic acid residue at position 1008 is replaced by an arginine residue (E1008R). In some embodiments, the glutamic acid residue at position 1008 is replaced by a lysine residue (E1008K). In some embodiments, the glutamic acid residue at position 1008 is replaced by a nonpolar or small polar amino acid residue. In some embodiments, the glutamic acid residue at position 1008 is replaced by a phenylalanine residue (E1008F). In some embodiments, the glutamic acid residue at position 1008 is replaced by a tryptophan residue (E1008W). In some embodiments, the glutamic acid residue at position 1008 is replaced by a glycine residue (E1008G). In some embodiments, the glutamic acid residue at position 1008 is replaced by an isoleucine residue (E1008I). In some embodiments, the glutamic acid residue at position 1008 is replaced by a valine residue (E1008V). In some embodiments, the glutamic acid residue at position 1008 is replaced by a proline residue (E1008P). In some embodiments, the glutamic acid residue at position 1008 is replaced by a serine residue (E1008S). In other embodiments, the glutamic acid residue at position 1008 is replaced by an asparagine residue (E1008N). In other embodiments, the glutamic acid residue at position 1008 is replaced by an alanine residue (E1008A). In other embodiments, the glutamic acid residue at position 1008 is replaced by a Methionine residue (E1008M). In some embodiments, the glutamic acid residue at position 1008 is replaced by a leucine residue (E1008L).

In some embodiments, to improve editing efficiency, the adenosine deaminase may comprise one or more of the mutations: E1007S, E1007A, E1007V, E1008Q, E1008R, E1008H, E1008M, E1008N, E1008K, based on amino acid sequence positions of hADAR1-D, and mutations in a homologous ADAR protein corresponding to the above.

In some embodiments, to reduce editing efficiency, the adenosine deaminase may comprise one or more of the mutations: E1007R, E1007K, E1007Y, E1007L, E1007T, E1008G, E1008I, E1008P, E1008V, E1008F, E1008W, E1008S, E1008N, E1008K, based on amino acid sequence positions of hADAR1-D, and mutations in a homologous ADAR protein corresponding to the above.

In some embodiments, the substrate editing preference, efficiency and/or selectivity of an adenosine deaminase is affected by amino acid residues near or in the active center of the enzyme. In some embodiments, the adenosine deaminase comprises a mutation at the glutamic acid 1008 position in hADAR1-D sequence, or a corresponding position in a homologous ADAR protein. In some embodiments, the mutation is E1008R, or a corresponding mutation in a homologous ADAR protein. In some embodiments, the E1008R mutant has an increased editing efficiency for target adenosine residue that has a mismatched G residue on the opposite strand.

In some embodiments, the adenosine deaminase protein further comprises or is connected to one or more double-stranded RNA (dsRNA) binding motifs (dsRBMs) or domains (dsRBDs) for recognizing and binding to double-stranded nucleic acid substrates. In some embodiments, the interaction between the adenosine deaminase and the double-stranded substrate is mediated by one or more additional protein factor(s), including a CRISPR/CAS protein factor. In some embodiments, the interaction between the adenosine deaminase and the double-stranded substrate is further mediated by one or more nucleic acid component(s), including a guide RNA.

According to the present invention, the substrate of the adenosine deaminase is an RNA/DNA heteroduplex formed upon binding of the guide molecule to its DNA target which then forms the CRISPR-Cas complex with the CRISPR-Cas enzyme. The RNA/DNA or DNA/RNA heteroduplex is also referred to herein as the "RNA/DNA hybrid", "DNA/RNA hybrid" or "double-stranded substrate". The particular features of the guide molecule and CRISPR-Cas enzyme are detailed below.

The term "editing selectivity" as used herein refers to the fraction of all sites on a double-stranded substrate that is edited by an adenosine deaminase. Without being bound by theory, it is contemplated that editing selectivity of an adenosine deaminase is affected by the double-stranded substrate's length and secondary structures, such as the presence of mismatched bases, bulges and/or internal loops.

In some embodiments, when the substrate is a perfectly base-paired duplex longer than 50 bp, the adenosine deaminase may be able to deaminate multiple adenosine residues within the duplex (e.g., 50% of all adenosine residues). In some embodiments, when the substrate is shorter than 50 bp, the editing selectivity of an adenosine deaminase is affected by the presence of a mismatch at the target adenosine site. Particularly, in some embodiments, adenosine (A) residue having a mismatched cytidine (C) residue on the opposite strand is deaminated with high efficiency. In some embodiments, adenosine (A) residue having a mismatched guanosine (G) residue on the opposite strand is skipped without editing.

CRISPR-Cas Modification

In some embodiments, a polynucleotide of the present invention described elsewhere herein can be modified using a CRISPR-Cas and/or Cas-based system.

In general, a CRISPR-Cas or CRISPR system as used in herein and in documents, such as International Patent Publication No. WO 2014/093622 (PCT/US2013/074667), refers collectively to transcripts and other elements involved in the expression of or directing the activity of CRISPR-associated ("Cas") genes, including sequences encoding a Cas gene, a tracr (transactivating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.mol-cel.2015.10.008.

CRISPR-Cas systems can generally fall into two classes based on their architectures of their effector molecules, which are each further subdivided by type and subtype. The two classes are Class 1 and Class 2. Class 1 CRISPR-Cas systems have effector modules composed of multiple Cas proteins, some of which form crRNA-binding complexes, while Class 2 CRISPR-Cas systems include a single, multi-domain crRNA-binding protein.

In some embodiments, the CRISPR-Cas system that can be used to modify a polynucleotide of the present invention described herein can be a Class 1 CRISPR-Cas system. In some embodiments, the CRISPR-Cas system that can be used to modify a polynucleotide of the present invention described herein can be a Class 2 CRISPR-Cas system.

Class 1 CRISPR-Cas Systems

In some embodiments, the CRISPR-Cas system that can be used to modify a polynucleotide of the present invention described herein can be a Class 1 CRISPR-Cas system. Class 1 CRISPR-Cas systems are divided into types I, II, and IV. Makarova et al. 2020. Nat. Rev. 18: 67-83, particularly as described in FIG. 1. Type I CRISPR-Cas systems are divided into 9 subtypes (I-A, I-B, I-C, I-D, I-E, I-F1, I-F2, I-F3, and IG). Makarova et al., 2020. Class 1, Type I CRISPR-Cas systems can contain a Cas3 protein that can have helicase activity. Type III CRISPR-Cas systems are divided into 6 subtypes (III-A, III-B, III-E, and III-F). Type III CRISPR-Cas systems can contain a Cas10 that can include an RNA recognition motif called Palm and a cyclase domain that can cleave polynucleotides. Makarova et al., 2020. Type IV CRISPR-Cas systems are divided into 3 subtypes. (IV-A, IV-B, and IV-C). Makarova et al., 2020. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al. 2018. The CRISPR Journal, v. 1, n5, FIG. 5.

The Class 1 systems typically comprise a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g., Cas 4, DNA nuclease), CRISPR associated Rossman fold (CARF) domain containing proteins, and/or RNA transcriptase.

The backbone of the Class 1 CRISPR-Cas system effector complexes can be formed by RNA recognition motif domain-containing protein(s) of the repeat-associated mysterious proteins (RAMPs) family subunits (e.g., Cas 5, Cas6, and/or Cas7). RAMP proteins are characterized by having one or more RNA recognition motif domains. In some embodiments, multiple copies of RAMPs can be present. In some embodiments, the Class I CRISPR-Cas system can include 1, 2, 3, 4, 5, 6, 7, 8, 9, 10, 11, 12 or more Cas5, Cas6, and/or Cas 7 proteins. In some embodiments, the Cas6 protein is an RNAse, which can be responsible for pre-crRNA processing. When present in a Class 1 CRISPR-Cas system, Cas6 can be optionally physically associated with the effector complex.

Class 1 CRISPR-Cas system effector complexes can, in some embodiments, also include a large subunit. The large subunit can be composed of or include a Cas8 and/or Cas10 protein. See, e.g., FIGS. 1 and 2. Koonin E V, Makarova K S. 2019. Phil. Trans. R. Soc. B 374: 20180087, DOI: 10.1098/rstb.2018.0087 and Makarova et al. 2020.

Class 1 CRISPR-Cas system effector complexes can, in some embodiments, include a small subunit (for example, Cash 1). See, e.g., FIGS. 1 and 2. Koonin E V, Makarova K S. 2019 Origins and Evolution of CRISPR-Cas systems. Phil. Trans. R. Soc. B 374: 20180087, DOI: 10.1098/rstb.2018.0087.

In some embodiments, the Class 1 CRISPR-Cas system can be a Type I CRISPR-Cas system. In some embodiments, the Type I CRISPR-Cas system can be a subtype I-A CRISPR-Cas system. In some embodiments, the Type I CRISPR-Cas system can be a subtype I-B CRISPR-Cas system. In some embodiments, the Type I CRISPR-Cas system can be a subtype I-C CRISPR-Cas system. In some embodiments, the Type I CRISPR-Cas system can be a subtype I-D CRISPR-Cas system. In some embodiments, the Type I CRISPR-Cas system can be a subtype I-E CRISPR-Cas system. In some embodiments, the Type I CRISPR-Cas system can be a subtype I-F1 CRISPR-Cas system. In some embodiments, the Type I CRISPR-Cas system can be a subtype I-F2 CRISPR-Cas system. In some embodiments, the Type I CRISPR-Cas system can be a subtype I-F3 CRISPR-Cas system. In some embodiments, the Type I CRISPR-Cas system can be a subtype I-G CRISPR-Cas system. In some embodiments, the Type I CRISPR-Cas system can be a CRISPR Cas variant, such as a Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems as previously described.

In some embodiments, the Class 1 CRISPR-Cas system can be a Type III CRISPR-Cas system. In some embodiments, the Type III CRISPR-Cas system can be a subtype III-A CRISPR-Cas system. In some embodiments, the Type III CRISPR-Cas system can be a subtype III-B CRISPR-Cas system. In some embodiments, the Type III CRISPR-Cas system can be a subtype III-C CRISPR-Cas system. In some embodiments, the Type III CRISPR-Cas system can be a subtype III-D CRISPR-Cas system. In some embodiments, the Type III CRISPR-Cas system can be a subtype III-E CRISPR-Cas system. In some embodiments, the Type III CRISPR-Cas system can be a subtype III-F CRISPR-Cas system.

In some embodiments, the Class 1 CRISPR-Cas system can be a Type IV CRISPR-Cas-system. In some embodiments, the Type IV CRISPR-Cas system can be a subtype IV-A CRISPR-Cas system. In some embodiments, the Type IV CRISPR-Cas system can be a subtype IV-B CRISPR-Cas system. In some embodiments, the Type IV CRISPR-Cas system can be a subtype IV-C CRISPR-Cas system.

The effector complex of a Class 1 CRISPR-Cas system can, in some embodiments, include a Cas3 protein that is optionally fused to a Cas2 protein, a Cas4, a Cas5, a Cas6, a Cas7, a Cas8, a Cas10, a Cas11, or a combination thereof. In some embodiments, the effector complex of a Class 1 CRISPR-Cas system can have multiple copies, such as 1, 2, 3, 4, 5, 6, 7, 8, 9, 10, 11, 12, 13, or 14, of any one or more Cas proteins.

Class 2 CRISPR-Cas Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at FIG. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1(V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), Cas12d (CasY), Cas12e (CasX), and/or Cas14.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

Specialized Cas-Based Systems

In some embodiments, the system is a Cas-based system that is capable of performing a specialized function or activity. For example, the Cas protein may be fused, operably coupled to, or otherwise associated with one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence specific targeting functionality that delivers the functional domain to or proximate a target sequence. Example functional domains that may be fused to, operably coupled to, or otherwise associated with a Cas protein can be or include, but are not limited to a nuclear localization signal (NLS) domain, a nuclear export signal (NES) domain, a translational activation domain, a transcriptional activation domain (e.g. VP64, p65, MyoD1, HSF1, RTA, and SETT/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof. Methods for generating catalytically dead Cas9 or a nickase Cas9 (WO 2014/204725, Ran et al. Cell. 2013 Sep. 12; 154(6):1380-1389), Cas12 (Liu et al. Nature Communications, 8, 2095 (2017), and Cas13 (International Patent Publication Nos. WO 2019/005884 and WO2019/060746) are known in the art and incorporated herein by reference.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some embodiments, all of the functional domains are different from each other. In some embodiments, at least two of the functional domains are different from each other. In some embodiments, at least two of the functional domains are the same as each other.

Other suitable functional domains can be found, for example, in International Patent Publication No. WO 2019/018423.

Split CRISPR-Cas Systems

In some embodiments, the CRISPR-Cas system is a split CRISPR-Cas system. See e.g., Zetche et al., 2015. Nat. Biotechnol. 33(2): 139-142 and International Patent Publication WO 2019/018423, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

DNA and RNA Base Editing

In some embodiments, a polynucleotide of the present invention described elsewhere herein can be modified using a base editing system. In some embodiments, a Cas protein is connected or fused to a nucleotide deaminase. Thus, in some embodiments the Cas-based system can be a base editing system. As used herein, "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA binding Cas protein such as, but not limited to, Class 2 Type II and Type V systems. Two classes of DNA base editors are generally known: cytosine base editors (CBEs) and adenine base editors (ABEs). CBEs convert a C•G base pair into a T•A base pair (Komor et al. 2016. Nature. 533:420-424; Nishida et al. 2016. Science. 353; and Li et al. Nat. Biotech. 36:324-327) and ABEs convert an A•T base pair to a G•C base pair. Collectively, CBEs and ABEs can mediate all four possible transition mutations (C to T, A to G, T to C, and G to A). Rees and Liu. 2018. Nat. Rev. Genet. 19(12): 770-788, particularly at FIGS. 1b, 2a-2c, 3a-3f, and Table 1. In some embodiments, the base editing system includes a CBE and/or an ABE. In some embodiments, a polynucleotide of the present invention described elsewhere herein can be modified using a base editing system. Rees and Liu. 2018. Nat. Rev. Gent. 19(12):770-788. Base editors also generally do not need a DNA donor template and/or rely on homology-directed repair. Komor et al. 2016. Nature. 533: 420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature. 533:420-424; Nishida et al. 2016. Science. 353; and Gaudeli et al. 2017. Nature. 551:464-471.

Other Example Type V base editing systems are described in International Patent Publication Nos. WO 2018/213708, WO 2018/213726, and International Patent Applications No. PCT/US2018/067207, PCT/US2018/067225, and PCT/US2018/067307, each of which is incorporated herein by reference.

In certain example embodiments, the base editing system may be an RNA base editing system. As with DNA base editors, a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA base editor may be used to delete or introduce a post-translation modification site in the expressed mRNA. In contrast to DNA base editors, whose edits are permanent in the modified cell, RNA base editors can provide edits where finer, temporal control may be needed, for example in modulating a particular immune response. Example Type VI RNA-base editing systems are described in Cox et al. 2017. Science 358: 1019-1027, International Patent Publication Nos. WO 2019/005884, WO 2019/005886, and WO 2019/071048, and International Patent Application Nos. PCT/US20018/05179 and PCT/US2018/067207, which are incorporated herein by reference. An example FnCas9 system that may be adapted for RNA base editing purposes is described in International Patent Publication No. WO 2016/106236, which is incorporated herein by reference.

An example method for delivery of base-editing systems, including use of a split-intein approach to divide CBE and ABE into reconstitutable halves, is described in Levy et al. Nature Biomedical Engineering doi.org/10.1038/s41441-019-0505-5 (2019), which is incorporated herein by reference.

Prime Editors

In some embodiments, a polynucleotide of the present invention described elsewhere herein can be modified using a prime editing system. See e.g. Anzalone et al. 2019. Nature. 576: 149-157. Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion and combinations thereof. Generally, a prime editing system, as exemplified by PE1, PE2, and PE3 (Id.), can include a reverse transcriptase fused or otherwise coupled or associated with an RNA-programmable nickase and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRIPSR-Cas systems along with few byproducts and greater or similar efficiency as compared to traditional CRISPR-Cas systems.

In some embodiments, the prime editing guide molecule can specify both the target polynucleotide information (e.g., sequence) and contain a new polynucleotide cargo that replaces target polynucleotides. To initiate transfer from the guide molecule to the target polynucleotide, the PE system can nick the target polynucleotide at a target side to expose a 3'hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576: 149-157, particularly at FIGS. 1b, 1c, related discussion, and Supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

In some embodiments, the prime editing system can be a PE1 system or variant thereof, a PE2 system or variant thereof, or a PE3 (e.g. PE3, PE3b) system. See e.g., Anzalone et al. 2019. Nature. 576: 149-157, particularly at pgs. 2-3, FIGS. 2a, 3a-3f, 4a-4b, Extended data FIGS. 3a-3b, 4.

The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576: 149-157, particularly at pg. 3, FIG. 2a-2b, and Extended Data FIGS. 5a-c.

CRISPR Associated Transposase (CAST) Systems

In some embodiments, a polynucleotide of the present invention described elsewhere herein can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on host cell repair machinery. CAST systems can be Class1 or Class 2 CAST systems. An example Class 1 system is described in Klompe et al. Nature, doi: 10.1038/s41586-019-1323, which is in incorporated herein by reference. An example Class 2 system is described in Strecker et al. Science. 10/1126/science. aax9181 (2019), and PCT/US2019/066835 which are incorporated herein by reference.

Guide Molecules

The CRISPR-Cas or Cas-Based system described herein can, in some embodiments, include one or more guide molecules. The terms guide molecule, guide sequence and guide polynucleotide refer to polynucleotides capable of guiding Cas to a target genomic locus and are used interchangeably as in foregoing cited documents such as International Patent Publication No. WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36(4)702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net).

A guide sequence, and hence a nucleic acid-targeting guide, may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it being advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in International Patent Application No. PCT US2019/045582, specifically paragraphs [0178]-[0333]. which is incorporated herein by reference.

Target Sequences, PAMs, and PFSs

Target Sequences

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16(4):504-517. Table 1 (from Gleditzsch et al. 2019) below shows several Cas polypeptides and the PAM sequence they recognize.

TABLE 1

Example PAM Sequences

| Cas Protein | PAM Sequence |
|---|---|
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cas12a (Cpf1) (including LbCp1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein H is A, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523(7561):481-5. doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi: http://dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155(Pt. 3):733-740; Atschul et al. 1990. J. Mol. Biol. 215:403-410; Biswass et al. 2013 RNA Biol. 10:817-827; and Grissa et al. 2007. Nucleic Acid Res. 35:W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016. Mol. Cell. 16:253), and negative screening (Zetsche et al. 2015. Cell. 163:759-771).

As previously mentioned, CRISPR-Cas systems that target RNA do not typically rely on PAM sequences. Instead such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from *Leptotrichia shahii* (LShCAs13a) have a specific discrimination against G at the 3'end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16(4):504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16(4):504-517.

Overall Type VI CRISPR-Cas systems appear to have less restrictive rules for substrate (e.g., target sequence) recognition than those that target DNA (e.g., Type V and type II).

Zinc Finger Nucleases

In some embodiments, the polynucleotide is modified using a Zinc Finger nuclease or system thereof. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to FokI cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Sequences Related to Nucleus Targeting and Transportation

In some embodiments, one or more components (e.g., the Cas protein and/or deaminase) in the composition for engineering cells may comprise one or more sequences related to nucleus targeting and transportation. Such sequence may facilitate the one or more components in the composition for targeting a sequence within a cell. In order to improve targeting of the CRISPR-Cas protein and/or the nucleotide deaminase protein or catalytic domain thereof used in the methods of the present disclosure to the nucleus, it may be advantageous to provide one or both of these components with one or more nuclear localization sequences (NLSs).

In some embodiments, the NLSs used in the context of the present disclosure are heterologous to the proteins. Non-limiting examples of NLSs include an NLS sequence derived from: the NLS of the SV40 virus large T-antigen, having the amino acid sequence PKKKRKV (SEQ ID NO:1) or PKKKRKVEAS (SEQ ID NO:2); the NLS from nucleoplasmin (e.g., the nucleoplasmin bipartite NLS with the sequence KRPAATKKAGQAKKKK (SEQ ID NO:3)); the c-myc NLS having the amino acid sequence PAAKRVKLD (SEQ ID NO:4) or RQRRNELKRSP (SEQ ID NO:5); the hRNPA1 M9 NLS having the sequence NQSSNFGPMKGGNFGGRSSGPYGGGGQYFAK-PRNQGGY (SEQ ID NO:6); the sequence RMRIZFKNKGKDTAELRRRRVEVSVELRKAKKD-EQILKRRNV (SEQ ID NO:7) of the IBB domain from importin-alpha; the sequences VSRKRPRP (SEQ ID NO:8) and PPKKARED (SEQ ID NO:9) of the myoma T protein; the sequence PQPKKKPL (SEQ ID NO:10) of human p53; the sequence SALIKKKKKMAP (SEQ ID NO:11) of mouse c-abl IV; the sequences DRLRR (SEQ ID NO:12) and PKQKKRK (SEQ ID NO:13) of the influenza virus NS1; the sequence RKLKKKIKKL (SEQ ID NO:14) of the Hepatitis virus delta antigen; the sequence REKKKFLKRR (SEQ ID NO:15) of the mouse Mx1 protein; the sequence KRKGDEVDGVDEVAKKKSKK (SEQ ID NO:16) of the human poly(ADP-ribose) polymerase; and the sequence RKCLQAGMNLEARKTKK (SEQ ID NO:17) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting), as compared to a control not exposed to the CRISPR-Cas protein and deaminase protein, or exposed to a CRISPR-Cas and/or deaminase protein lacking the one or more NLSs.

The CRISPR-Cas and/or nucleotide deaminase proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the CRISPR-Cas proteins, an NLS attached to the C-terminal of the protein.

In certain embodiments, the CRISPR-Cas protein and the deaminase protein are delivered to the cell or expressed within the cell as separate proteins. In these embodiments, each of the CRISPR-Cas and deaminase proteins can be provided with one or more NLSs as described herein. In certain embodiments, the CRISPR-Cas and deaminase proteins are delivered to the cell or expressed with the cell as a fusion protein. In these embodiments one or both of the CRISPR-Cas and deaminase protein is provided with one or more NLSs. Where the nucleotide deaminase is fused to an adaptor protein (such as MS2) as described above, the one or more NLS can be provided on the adaptor protein, provided that this does not interfere with aptamer binding. In particular embodiments, the one or more NLS sequences may also function as linker sequences between the nucleotide deaminase and the CRISPR-Cas protein.

In certain embodiments, guides of the disclosure comprise specific binding sites (e.g. aptamers) for adapter proteins, which may be linked to or fused to a nucleotide deaminase or catalytic domain thereof. When such a guide forms a CRISPR complex (e.g., CRISPR-Cas protein binding to guide and target), the adapter proteins bind and the nucleotide deaminase or catalytic domain thereof associated with the adapter protein is positioned in a spatial orientation which is advantageous for the attributed function to be effective.

The skilled person will understand that modifications to the guide which allow for binding of the adapter+nucleotide deaminase, but not proper positioning of the adapter+ nucleotide deaminase (e.g. due to steric hindrance within the three-dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and in some cases at both the tetra loop and stem loop 2.

In some embodiments, a component (e.g., the dead Cas protein, the nucleotide deaminase protein or catalytic domain thereof, or a combination thereof) in the systems may comprise one or more nuclear export signals (NES), one or more nuclear localization signals (NLS), or any combinations thereof. In some cases, the NES may be an HIV Rev NES. In certain cases, the NES may be MAPK NES. When the component is a protein, the NES or NLS may be at the C terminus of component. Alternatively or additionally, the NES or NLS may be at the N terminus of component. In some examples, the Cas protein and optionally said nucleotide deaminase protein or catalytic domain thereof comprise one or more heterologous nuclear export signal(s) (NES(s)) or nuclear localization signal(s) (NLS(s)), preferably an HIV Rev NES or MAPK NES, preferably C-terminal.

Templates

In some embodiments, the composition for engineering cells comprise a template, e.g., a recombination template. A template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cas protein mediated cleavage event. In an embodiment, the template nucleic acid may include a sequence that corresponds to both, a first site on the target sequence that is cleaved in a first Cas protein mediated event, and a second site on the target sequence that is cleaved in a second Cas protein mediated event.

In certain embodiments, the template nucleic acid can include a sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include a sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include a sequence which, when integrated, results in decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include a sequence which results in a change in sequence of 1, 2, 3, 4, 5, 6, 7, 8, 9, 10, 11, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 110+/−20, 120+/−20, 130+/−20, 140+/−20, 150+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the disclosure can be constructed using recombinant techniques (see, for example, Sambrook et al., 2001 and Ausubel et al., 1996).

In certain embodiments, a template nucleic acid for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Suzuki et al. describe in vivo genome editing via CRISPR/Cas9 mediated homology-independent targeted integration (2016, Nature 540:144-149).

TALE Systems

As disclosed herein editing can be made by way of the transcription activator-like effector nucleases (TALENs) system. Accordingly, In some embodiments, a TALE nuclease or TALE nuclease system can be used to modify a polynucleotide. In some embodiments, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-$(X_{12}X_{13})$-$X_{14-33}$ or $_{34}$ or $_{35}$, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}$-$(X_{12}X_{13})$-$X_{14-33}$ or $_{34}$ or $_{35})_z$, where in an advantageous embodiment, z is at least 5 to 40. In a further advantageous embodiment, z is at least 10 to 26.

The TALE monomers can have a nucleotide binding affinity that is determined by the identity of the amino acids in its RVD. For example, polypeptide monomers with an RVD of NI can preferentially bind to adenine (A), monomers with an RVD of NG can preferentially bind to thymine (T), monomers with an RVD of HD can preferentially bind to cytosine (C) and monomers with an RVD of NN can preferentially bind to both adenine (A) and guanine (G). In some embodiments, monomers with an RVD of IG can preferentially bind to T. Thus, the number and order of the polypeptide monomer repeats in the nucleic acid binding domain of a TALE determines its nucleic acid target specificity. In some embodiments, monomers with an RVD of NS can recognize all four base pairs and can bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011).

The polypeptides used in methods of the invention can be isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In some embodiments, polypeptide monomers having RVDs RN, NN, NK, SN, NH, KN, HN, NQ, HH, RG, KH, RH and SS can preferentially bind to guanine. In some embodiments, polypeptide monomers having RVDs RN, NK, NQ, HH, KH, RH, SS and SN can preferentially bind to guanine and can thus allow the generation of TALE polypeptides with high binding specificity for guanine containing target nucleic acid sequences. In some embodiments, polypeptide monomers having RVDs HH, KH, NH, NK, NQ, RH, RN and SS can preferentially bind to guanine and thereby allow the generation of TALE polypeptides with high binding specificity for guanine containing target nucleic acid sequences. In some embodiments, the RVDs that have high binding specificity for guanine are RN, NH RH and KH. Furthermore, polypeptide monomers having an RVD of NV can preferentially bind to adenine and guanine. In some embodiments, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full-length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ ID NO: 18)
M D P I R S R T P S P A R E L L S G P Q P D G V Q

P T A D R G V S P P A G G P L D G L P A R R T M S

R T R L P S P P A P S P A F S A D S F S D L L R Q

F D P S L F N T S L F D S L P P F G A H H T E A A

T G E W D E V Q S G L R A A D A P P P T M R V A V

T A A R P P R A K P A P R R R A A Q P S D A S P A

A Q V D L R T L G Y S Q Q Q Q E K I K P K V R S T

V A Q H H E A L V G H G F T H A H I V A L S Q H P

A A L G T V A V K Y Q D M I A A L P E A T H E A I

V G V G K Q W S G A R A L E A L L T V A G E L R G

P P L Q L D T G Q L L K I A K R G G V T A V E A V

H A W R N A L T G A P L N

An exemplary amino acid sequence of a C-terminal capping region is:

(SEQ ID NO: 19)
R P A L E S I V A Q L S R P D P A L A A L T N D H

L V A L A C L G G R P A L D A V K K G L P H A P A

L I K R T N R R I P E R T S H R V A D H A Q V V R

V L G F F Q C H S H P A Q A F D D A M T Q F G M S

R H G L L Q L F R R V G V T E L E A R S G T L P P

A S Q R W D R I L Q A S G M K R A K P S P T S T Q

T P D Q A S L H A F A D S L E R D L D A P S P M H

E G D Q T R A S

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full-length capping region, while fragments that include the C-terminal 20 amino acids retain greater than 50% of the efficacy of the full-length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies can be generated by any of a number of computer programs known in the art, which include but are not limited to BLAST or FASTA. Suitable computer programs for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In some embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments, the effector domain is an enhancer of transcription (i.e., an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163, 514; 8,133,697; 8,021,867; 8,119,361; 8,119,381; 8,124, 369; and 8,129,134, which are specifically incorporated by reference.

RNA Interference

In certain embodiments, the genetic modifying agent is RNAi (e.g., shRNA). As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene. Antisense RNA is single stranded RNA that is complementary to a protein coding messenger RNA (mRNA) with which it hybridizes, and can block mRNA translation.

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), ribozymes, and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112; Burnett and Rossi (2012) Chem Biol. 19 (1):60-71; and WO2015130968, which is incorporated herein by reference in its entirety.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range there within.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 8,604,192; 8,697,663; 8,703,728; 8,796,437; 8,865,677; and 8,883,752 each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2'

O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

Delivery

The programmable nucleic acid modifying agents and other modulating agents, or components thereof, or nucleic acid molecules thereof (including, for instance HDR template), or nucleic acid molecules encoding or providing components thereof, may be delivered by a delivery system herein described.

Vector delivery, e.g., plasmid, viral delivery: the modulating agents, can be delivered using any suitable vector, e.g., plasmid or viral vectors, such as adeno associated virus (AAV), lentivirus, adenovirus or other viral vector types, or combinations thereof. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Identifying Cell Types

Identifying cell types and/or cell phenotypes can comprise utilizing morphologic classifiers for identification as described elsewhere herein. The signature as defined herein (being it a phenotypic signature, gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to aid building of morphologic classifiers that can then be used to identify or suggest, for instance, particular therapies, or to follow up treatment, or to suggest ways to modulate immune systems. In embodiments, the methods may further comprise retraining the network to extract morphological signatures from individual cells treated with different drugs or perturbations and compute the intensity of this vector across time- and dose-points.

As used herein, "cell state" is used to describe elements of a cell's identity, type or subtype. Cell state can be thought of as the characteristic profile or phenotype of a cell, which can be transient or permanent. Cell states can arise transiently during a process that can occur over a period of time. Temporal progression from one cell state to another can be unidirectional (e.g., during differentiation, or following an environmental stimulus) or can be in a state of vacillation that is not necessarily unidirectional and in which the cell may return to the origin state. Vacillating processes can be oscillatory (e.g., cell-cycle or circadian rhythm) or can transition between states with no predefined order (e.g., due to stochastic, or environmentally controlled, molecular events). These processes may occur transiently within a stable cell type (such as in a transient environmental response), or may lead to a new, distinct type (such as in differentiation). Wagner et al., 2016. Nat Biotechnol. 34(111): 1145-1160.

The signatures of the present invention may be discovered by analysis of expression profiles of single-cells within a population of cells from isolated samples prior to use as a living biosensor, or in building morphologic classifiers pertinent to a particular illness (e.g. tumor samples), or analysis of label free imaging with or without perturbation, thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample or by applying the developed methodologies to label-free imaging of the cells with or without perturbation. Not being bound by a theory the signatures of the present invention may be microenvironment specific, such as their expression in a particular spatio-temporal context. Not being bound by a theory, signatures as discussed herein can be specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment or drug therapy. The signature may indicate the presence of one particular cell type. In one embodiment, the novel signatures are used to detect multiple cell states or hierarchies that occur in subpopulations of cancer cells that are linked to particular pathological condition (e.g. cancer grade), or linked to a particular outcome or progression of the disease (e.g. metastasis), or linked to a particular response to treatment of the disease.

As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

In further aspects, the invention relates to phenotypic signatures, gene signatures, protein signatures, and/or other genetic or epigenetic signatures of particular cell subpopulations, as defined herein elsewhere. The invention hereto also further relates to particular cell subpopulations, which may be identified based on the methods according to the invention as discussed herein; as well as methods to obtain such cell (sub)populations and screening methods to identify agents capable of inducing or suppressing particular cell (sub)populations.

Gene signatures and/or gene modules that are uniquely associated with cell types and subtypes, including in normal and in dysfunctional cell states, and molecular nodes that control them and can be analyzed and can uniquely identify a particular cell state (e.g. normal or dysfunctional) and/or type can be utilized in identifying cell types. In some embodiments, the biomarkers, signatures, and/or molecular targets described herein can be used to evaluate microenvironments and response, such as to specifically evaluate and target a dysfunctional state while leaving normal activation programs intact.

Single Cell Sequencing

In certain embodiments, single cell sequencing is utilized to collect data from samples and integrate the information with microscopy. In one approach, the information can be utilized, for example, to identify optimal cell type-specific markers to be used to stain images to generate a ground-truth training set. Different methods of single sequencing are better suited for sequencing certain samples (e.g., neurons, rare samples may be more optimally sequenced with a plate-based method or single nuclei sequencing).

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p 666-673, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi: 10.1038/nprot.2014.006).

In certain embodiments, the invention involves high-throughput single-cell RNA-seq. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: 10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; Gierahn et al., "Seq-Well: portable, low-cost RNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology"

bioRxiv 689273; doi: doi.org/10.1101/689273, all the contents and disclosure of each of which are herein incorporated by reference in their entirety In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "DivSeq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; International patent application number PCT/US2016/059239, published as WO2017164936 on Sep. 28, 2017; International patent application number PCT/US2018/060860, published as WO/2019/094984 on May 16, 2019; International patent application number PCT/US2019/055894, published as WO/2020/077236 on Apr. 16, 2020; and Drokhlyansky, et al., "The enteric nervous system of the human and mouse colon at a single-cell resolution," bioRxiv 746743; doi: 10.1101/746743, which are herein incorporated by reference in their entirety.

In certain embodiments, the invention involves the Assay for Transposase Accessible Chromatin using sequencing (ATAC-seq) as described. (see, e.g., Buenrostro, et al., Transposition of native chromatin for fast and sensitive epigenomic profiling of open chromatin, DNA-binding proteins and nucleosome position. Nature methods 2013; 10 (12): 1213-1218; Buenrostro et al., Single-cell chromatin accessibility reveals principles of regulatory variation. Nature523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4. doi: 10.1126/science.aab1601. Epub 2015 May 7; US20160208323A1; US20160060691A1; and WO2017156336A1). In certain example embodiments, assessing the cell (sub)types and states present in the ex vivo system may comprise analysis of expression matrices from the scRNA-seq data, performing dimensionality reduction, graph-based clustering and deriving list of cluster-specific genes in order to identify cell types and/or states present in the ex vivo system prior to and/or subsequent to perturbations. These marker genes may then be used throughout to relate the ex vivo system cell (sub)types and states to the system subsequent to perturbations for the purpose of verifying the training network. The same analysis may then be applied to the source material for the ex vivo cell-based system. From both sets of sc-RNAseq analysis an initial distribution of gene expression data is obtained. In certain embodiments, the distribution may be a count-based metric for the number of transcripts of each gene present in a cell. Further the clustering and gene expression matrix analysis allow for the identification of key genes in the initial ex vivo system and the perturbed ex vivo system, such as differences in the expression of key transcription factors. In certain example embodiments, this may be done conducting differential expression analysis. This may also be used to correlate certain gene markers or signatures to morphologic differences in the cells when imaged.

Methods of Generating Living Biosensor Systems

Methods of generating a living biosensor cell model is provided in certain embodiments, which may comprise distributing a sample of cells into one or more individual discrete volumes as described elsewhere herein. The sample can be obtained in one aspect direct from the subject using containers and kits described herein, from clinical settings, or biopsies. Generation of the living biosensor systems may comprise perturbing one or more of the individual discrete volumes with one or more agents; and identifying cell types and/or cell phenotypes of the sample at a single cell resolution over a period of time. As described herein, identifying the cell types and/or cell phenotypes can comprise utilizing morphologic classifiers, wherein the morphologic classifiers can be built using a convolutional neural network. Generating a living biosensor cell model can further comprise utilizing methods identifying cell phenotypes which can comprise characterizing perturbation-induced cellular death and non-perturbation induced cellular death.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants.

For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating the support with a liquid suspension containing the cells. The living biosensor systems can be imaged continuously and directly on the solid supports. Such impregnated supports can also be re-cultured by immersing them in a liquid culture medium.

The cells or cell populations in the systems can be cultured in a manner that permits them to survive, grow, propagate and/or differentiate towards desired cell types (e.g. differentiation) or cell states.

Diagnostic Methods

Diagnostic methods can be utilized with the living biosensor systems disclosed herein. In an aspect, methods of monitoring a subject in need thereof are provided. In one embodiment, the perturbations monitor drug sensitivity in a subject in need thereof, and may comprise detecting the drug sensitivity of the cells according to any one of the methods disclosed herein in a sample obtained from the subject. Detecting perturbations, including drug sensitivity may be accomplished in certain aspects by performing methods as disclosed herein in two or more samples obtained from the subject for at least two time points. For example, at least one sample can be obtained from a subject before treatment, and/or at least one sample can be obtained from a subject after treatment. Methods may comprise comparing the drug sensitivity or responsiveness to other perturbations of the two samples to inform the course of treatment. In an aspect, Methods may comprise monitoring of each sample occurs over a time window of less than about 10 days, less than about 5 days, or less than about 72 hours after perturbing the cells. Accordingly, use of the cell-based systems may comprise identifying a therapeutic agent or determining the efficacy of a therapeutic agent. Use of the cell-based system may comprise selecting one or more therapeutic agents for treatment of a subject in need thereof, or for screening agents having antitumor activity.

The terms "diagnosis" and "monitoring" are commonplace and well-understood in medical practice. By means of further explanation and without limitation the term "diagnosis" generally refers to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The methods and living biosensors of the present invention are useful in methods of identifying patient populations at risk or suffering from a cancer or other immune response based on the imaging and detection of cell types/phenotypes and their susceptibility and/or viability to particular perturbations. The living biosensors are also useful in monitoring subjects undergoing treatments and therapies for suitable or aberrant response(s) to determine efficaciousness of the treatment or therapy and for selecting or modifying therapies and treatments that would be efficacious in treating, delaying the progression of or otherwise ameliorating a symptom. The methodologies provided herein are useful for selecting a group of patients at a specific state of a disease with accuracy that facilitates selection of treatments.

The term "monitoring" generally refers to the follow-up of a disease or a condition in a subject for any changes which may occur over time.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Suitably, an altered quantity or phenotype in the ex vivo systems derived from the subject compared to a control subject having normal immune status or not having a disease indicates that the subject has an impaired immune status, a cancer, e.g. has a disease comprising an immune component or would benefit from an immune therapy.

Hence, the methods may rely on comparing the quantity of immune or tumor cell populations, drug susceptibility or other morphologic classifiers measured in samples from patients with reference values, wherein said reference values represent known predictions, diagnoses and/or prognoses of diseases or conditions as taught herein.

For example, distinct reference values may represent the prediction of a risk (e.g., an abnormally elevated risk) of having a given disease or condition as taught herein vs. the prediction of no or normal risk of having said disease or condition. In another example, distinct reference values may represent predictions of differing degrees of risk of having such disease or condition.

In a further example, distinct reference values can represent the diagnosis of a given disease or condition as taught herein vs. the diagnosis of no such disease or condition (such as, e.g., the diagnosis of healthy, or recovered from said disease or condition, etc.). In another example, distinct reference values may represent the diagnosis of such disease or condition of varying severity.

In yet another example, distinct reference values may represent a good prognosis for a given disease or condition as taught herein vs. a poor prognosis for said disease or condition. In a further example, distinct reference values may represent varyingly favourable or unfavourable prognoses for such disease or condition.

Such comparison may generally include any means to determine the presence or absence of at least one difference and optionally of the size of such difference between values being compared. A comparison may include a visual inspection, an arithmetical or statistical comparison of measurements. Such statistical comparisons include, but are not limited to, applying a rule.

Reference values may be established according to known procedures previously employed for other cell populations, biomarkers and gene or gene product signatures and/or morphologic classifiers. For example, a reference value may be established in an individual or a population of individuals characterised by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or ±1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

Screening for Modulating Agents

A further aspect of the invention relates to a method for identifying an agent capable of modulating one or more phenotypic aspects of a cell or cell population as disclosed herein, comprising: a) applying a candidate agent to the cell or cell population; b) detecting modulation of one or more phenotypic aspects of the cell or cell population by the candidate agent, thereby identifying the agent. The phenotypic aspects of the cell or cell population that is modulated may be a gene signature or biological program specific to a cell type or cell phenotype or phenotype specific to a population of cells (e.g., an inflammatory phenotype or suppressive immune phenotype). In certain embodiments, steps can include administering candidate modulating agents to cells, detecting identified cell (sub)populations for changes in signatures, or identifying relative changes in cell (sub) populations which may comprise detecting relative abundance of particular gene signatures.

The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of an immune cell or immune cell population may be modulated without substantially altering other (unintended, undesired) phenotypic aspect(s).

The term "agent" broadly encompasses any condition, substance or agent capable of modulating one or more phenotypic aspects of a cell or cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of a cell or cell population as disclosed herein in a method comprising applying the candidate agent to the cell or cell population (e.g., exposing the cell or cell population to the candidate agent or contacting the cell or cell population with the candidate agent) and observing whether the desired modulation takes place.

Agents may include any potential class of biologically active conditions, substances or agents, such as for instance antibodies, proteins, peptides, nucleic acids, oligonucleotides, small molecules, or combinations thereof, as described herein.

The methods of phenotypic analysis can be utilized for evaluating environmental stress and/or state, for screening of chemical libraries, and to screen or identify structural, syntenic, genomic, and/or organism and species variations. For example, a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value. By exposing cells, or fractions thereof, tissues, or even whole animals, to different members of the chemical libraries, and performing the methods described herein, different members of a chemical library can be screened for their effect on immune phenotypes thereof simultaneously in a relatively short amount of time, for example using a high throughput method.

In some embodiments, the disclosed methods can be used to screen chemical libraries for agents that modulate chromatin architecture epigenetic profiles, and/or relationships thereof.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures or biological programs of the present invention may be used to screen for drugs that reduce the signature or biological program in cells as described herein. The signature or biological program may be used for GE-HTS. In certain embodiments, pharmacological screens may be used to identify drugs that are selectively toxic to cells having a signature.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature or biological program of the present invention.

Pharmaceutical Compositions

The systems of the present invention may be utilized with various components to identify pharmaceutical compositions for therapy. The compositions may be combined with one or more pharmaceutically acceptable carriers or diluents to produce a pharmaceutical composition (which may be for human or animal use). Suitable carriers and diluents include, but are not limited to, isotonic saline solutions, for example phosphate-buffered saline. The composition of the invention may be administered by direct injection. The composition may be formulated for parenteral, intramuscular, intravenous, subcutaneous, intraocular, oral, transdermal administration, or injection into the spinal fluid.

A pharmaceutical composition refers to a composition that usually contains an excipient, such as a pharmaceutically acceptable carrier that is conventional in the art and that is suitable for administration to cells or to a subject. Pharmaceutically acceptable as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active components is well known in the art. Such materials should be non-toxic and should not interfere with desirable activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions which are to be administered orally or topically will usually not comprise cells, although it may be envisioned for oral compositions to also comprise cells, for example when gastro-intestinal tract indications are treated. Each of the cells or active components (e.g., modulants, immunomodulants, antigens) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

The pharmaceutical compositions may comprise a therapeutically effective amount of active components. The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregeletanized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

Kits

Kits including reagents, containers for the collection of samples, and materials for preparation and/or imaging of the living biosensor systems are also provided in embodiments of the presently disclosed subject matter. The kits can include instructions for the performing of diagnostics, reagents, and standards for calibrating or conducting the methods. The instructions provided in a kit according to the invention may be directed to suitable operational parameters in the form of a label or a separate insert. In embodiments, the kit can comprise containers according to the present disclosure for the aseptic collection of samples. In embodiments, the kit can comprise a container adapted to connect to the subject drain. The subject drain may comprise a port, catheter or other drain. Exemplary drains to which the container can be adapted to fit, or from which a direct to subject sample can be collected include percutaneously implanted catheters (tunneled, untunneled, central venous catheters), peritoneal ports, or peritoneovenous shunt. The kits may be direct to subject kits for collection a fresh sample comprising a container configured to collect the sample from a subject in an aseptic manner, instructions for collection and shipment of the sample, and a temperature control mechanism that maintains the integrity of the sample during shipment. Optionally, the kit may further comprise a standard or control information so that the test sample can be compared with the control information standard to determine if whether a consistent result is achieved.

Further embodiments are illustrated in the following Examples which are given for illustrative purposes only and are not intended to limit the scope of the invention.

EXAMPLES

Example 1

Pipeline of Living Samples

The ultimate goal of this technological development project is the generation of a robust, reproducible research-grade data generation pipeline that would ultimately enable Broad researchers to generate ex vivo small molecule dependency data on samples donated by cancer patients, including any hospital (to ensure inclusion of both common and rare tumors). While it may be possible someday in the future for such technology to be applied as a clinical diagnostic, Over the past two years, Applicants have built a patient-partnered pipeline for the acquisition of fresh, living cancer samples from across the United States without compromising quality or viability (FIG. 1). Briefly, patients provide consent via an online portal which triggers a real-time biologistics process spearheaded by colleagues at the Rare Cancer Research Foundation to deliver samples to the Broad Cell Line Factory. Thus far, 143 patients from 88 different institutions across 33 states have provided online consent and over 77 viable samples from patients with one of ~10 rare tumor types (from both large academic and community hospitals) have already arrived at the Broad. Applicants are currently obtaining 1-2 fresh gastroesophageal ascites samples per week and have optimized conditions for gastroesophageal cancer organoid derivation, maximizing cellular viability (current organoid success rate for such samples is >65%).

Applicants recognize that not all advanced cancer patients develop ascites and that the cancer cell fraction in ascites is highly variable (0.1%-20% based on work thus far). However, Applicants hypothesize that gastroesophageal ascites represents a strong starting point for this work for several reasons: (a) it represents advanced cancer where the need is greatest, (b) it obviates several key technical challenges related to tissue processing of solid tumors and is obtainable serially and in very high volumes (routinely >500 ml), (c) it retains multiple key cell types (including stroma, endothelial and immune) and (d) it enables such ex vivo living tissue studies to focus on validating genome-dependency predictions emerging from other Broad efforts.

The focus here is initially on advanced cancer. So, it will be helpful over time to compare ascites profiling to metastatic biopsy samples. But, the technical complexity of such profiling with such minute cell numbers while simultaneously requiring tissue disaggregation strategies is an immense Year 1 challenge. But, to begin to explore the generalizability of the approach and to ensure that the studies are not overfit to patient ascites, Applicants will also begin to explore the use of primary tumor and core biopsy samples from gastroesophageal cancer patients during feasibility testing phase. Specifically, single cell profiles of ascites samples will be compared to such solid tumors to ensure that similar cell types are represented. Applicants will also explore how various mechanical or enzymatic dissociation conditions affect cell viability.

This project is highly ambitious and requires the careful optimization and coordination of a series of sub-activities for it to achieve its stated goal. These include: (1) real-time biologistics to transfer living samples from patients to the Broad without compromising cellular viability; (2) optimized, platformized sample processing protocols to maximize cellular viability ex vivo in the laboratory; (3) real-time data collection protocols capable of (a) identifying cell types and (b) measuring cell viability over time in a complex mixture; and finally, (4) computational methods to distinguish perturbation-induced cellular death from non-perturbation-induced cellular death.

Thus far, there is confidence in the ability to do (1) and (2). Over the past two years, Applicants built a patient-partnered pipeline for the acquisition of fresh, living cancer samples from across the United States without compromising quality or viability (FIG. 1). Briefly, patients provide consent via an online portal which triggers a real-time biologistics process spearheaded by colleagues at the Rare Cancer Research Foundation to deliver samples to the Broad Cell Line Factory. Thus far, 143 patients from 88 different institutions across 33 states have provided online consent and over 77 viable samples from patients with one of ~10 rare tumor types (from both large academic and community hospitals) have already arrived at the Broad. Applicants are currently obtaining 1-2 fresh gastroesophageal ascites samples per week and have optimized conditions for gastroesophageal cancer organoid derivation, maximizing cellular viability (current organoid success rate for such samples is >65%).

Example 2

Classifying Cell Types and Cell States Present in Ascites Fluid

The initial aim of this project is to use brightfield microscopy to identify the cell types and their viability in patient samples. While cell types might be readily identified using end-point assays such as Cell Painting, conventional end-point assays to measure cell death at single cell resolution are likely to be insufficient for this project because different cell types and patient samples will have different rates of stress-related cell death ex vivo. Moreover, even live cell staining protocols can induce phototoxicity. Therefore, building will be upon recently published work (Christiansen et al 2018, Ounkomol et al, 2018) that demonstrates the potential of using a pre-trained convolutional neural network to predict fluorescence-labelled image features (e.g. cell type, cell death) from transmitted-light microscopy (e.g. brightfield, which can be collected in real-time) (FIG. 2C, 2D).

Here, Applicants followed the sample acquisition and processing flow depicted in FIG. 2a, processing 20 fresh and 20 cryopreserved ascites samples, integrating information from microscopy and single cell RNAseq data. First, Applicants performed sc-RNAseq on a limited number (~10) of samples to compare the cellular composition of fresh vs. cryopreserved samples with and without immune cell depletion (anti-CD45 pull-down). From this, Applicants\(a) determined whether cryopreservation impacts viability and (b) identifies optimal cell type-specific markers to be used to stain images to generate a ground-truth training dataset. In parallel, Applicants collected real-time brightfield microscopy data on the same samples followed by staining using cell type or cell state specific markers such as CD45 or caspase activity.

From this, morphologic classifiers will be built that distinguish cancer from immune from other cell types present in such mixtures and describe their viability. To do this, Applicants utilized the pre-trained in-silico labeling network from Christiansen et al, with several adaptations. The current algorithm takes a 3D stack of 16 brightfield or phase-contrast images and returns a set of 2D images, each representing one of the fluorescent dye channels that the network was initially trained to predict. Overall, the network contains 27 million trainable parameters. Applicants will use the published network and retrain it to predict fluorescent labels for CD45 immunofluorescence and CellEvent, a caspase reactive fluorescent marker (Applicants have recently begun to collect a series of training images spanning more than 200,000 images across 5 patient samples). Thus far, Applicants have successfully reproduced the findings by Christiansen et al. using published images from the authors. The next step is to retrain the network on new set of images comprising ground-truth fluorescent markers for immune cells (CD45) and apoptotic cells. The final goal is to adapt the network so it can identify the most abundant cell types and phenotypes, such as apoptosis. If successful in classifying high level cell types (e.g. malignant vs. immune vs. stromal vs. other), Applicants will access the network's embeddings for individual cells (see approach in Caicedo J C, McQuin C, Goodman A, Singh S, Carpenter A E (2018). Weakly supervised learning of single-cell feature embeddings. 2018 IEEE Conference on Computer Vision and Pattern Recognition (CVPR) bioRxiv p. 293431./doi: 10.1101/293431), to determine whether it is possible to identify additional cell subtypes and states.

An additional 10-20 samples will then be processed (both from additional patients, as well as serial samples from the same patients) to determine the robustness and generalizability of the cell type classifier. Applicants will also process an additional ~5 solid tumor samples (performing both single cell profiling and image collection) and explore how mechanical or enzymatic dissociation conditions impacts the subcellular composition as well as the feasibility of using the cell type classifier. If the classifier works well for ascites but fails for disaggregated tissue samples, a parallel project will be launched to build new classifiers for additional sample types. Overall, while the technical difficulty of an initial focus on solid tumors makes this aspect of the project challenging, a key milestone will be an assessment of the generalizability of the method to various sample types.

Where possible, Applicants will determine whether further optimization of plating, media and tissue processing conditions can reproducibly preserve viability and initial proliferation of cancer cells from multiple patients for at least 72 hours (see FIG. 2B for a pilot example).

Example 3

Use of Brightfield Microscopy to Classify Drug Sensitive from Insensitive Cells within Heterogeneous Mixtures Work will be extended towards the classification of drug sensitivity at the single cell level. The central hypothesis is while cells will undergo morphologic changes as a result of cell death without drugs, each drug will induce a supplemental drug or drug-class specific morphologic change that can be learned.

Briefly, Applicants will use the retrained network (perhaps with additional adaptations) to extract morphological signatures from individual cells treated with different drugs and compute the intensity of this vector across time- and dose-points. Applicants predict that neural networks will overestimate the drug dose/exposure time of a very sensitive patient sample and will underestimate the dose/exposure time of an insensitive sample.

Applicants have already collected preliminary data with the cytotoxic agent Staurosporine, but must extend this across samples and doses for further validation. If this result holds up, Applicants will extend to additional drugs with diverse mechanisms of action since Applicants expect that different drugs are likely to induce different "death morphologies" and individual samples will not all be sensitive to the same drugs. Applicants have prioritized a collection of eight drugs based on prior clinical knowledge as well as predictions from the Gastroesophageal Cancer Dependency Map project, including cytotoxic, targeted and immunity-inducing agents (Olaparib; PARP inhibitor, Afatanib; ERBB2-EGFR inhibitor, Trametinib; MEK inhibitor, Idasanutlin; MDM2 inhibitor, PD173073; FGFR inhibitor, Defactinib; FAK inhibitor, Paclitaxel; microtubule inhibitor, and Pembrolizumab; anti-PD1). Applicants have already arrayed seven of these drugs into assay-ready 384 well plates with 6 replicates of each drug arrayed at 8-point dose concentrations.

Applicants will expose approximately 10 samples to the drug matrix and collect brightfield imaging data at 6, 12, 24, 48 and 72 hours. Applicants will again compare with end point caspase staining to validate that morphology changes correspond to cell death and to determine which of these drugs can induce readily observable drug-induced morphologic changes (beyond control treated samples).

Finally, Applicants will benchmark these predictions in two ways. First, Applicants will utilize serial samples collected from the same patients (intra-patient controls) whose ascites was prospectively collected during anti-cancer therapy at roughly weekly intervals. Within a given patient Applicants expect to see little inter-sample variability, though evolutionary changes in drug sensitivity will be recorded and correlated with clinical response and histologic subtype. If Applicants are able to cryopreserve, batch analysis of previously collected serial samples will serve to minimize inter-sample and inter-run variations. Lastly, several of the samples in the historical cohort are already known to be clinically sensitive and/or resistant to agents on the 8-drug panel including taxanes, Pembrolizumab or ERBB2 inhibition, thus recapitulation of such results would be an interesting (although clearly optional) validation of this research pipeline.

Discussion

The ability to infer dependencies given the molecular features of a patient's tumor is central to cancer precision medicine. Ongoing clinical and laboratory efforts aim to develop reference data to improve the accuracy of such inferences, in part by correlating molecular features of patient tumors with therapeutic outcomes. While laboratory efforts can be systematic and unbiased, they are bounded both by the subset of human tumors that can be propagated as long-term cell models and by the inability to retain the cellular diversity of real tumors in such models. Here, Applicants took initial catalytic steps to make living, heterogeneous cancer tissues compatible with ex vivo functional genomics at the Broad. As an initial area of focus, Applicants attempted to use real-time microscopy to map cell types and drug response profiles of cancer cells in freshly obtained ascites fluid and primary tumor samples from gastroesophageal cancer patients at single cell resolution. This technical development work emphasizes the optimization and standardization of reproducible data generation and the computational inference of cell type and cellular death from label-free (transmitted light) microscopic images taken within 72 hours of sample receipt. To confirm predictions, Applicants will benchmark the results against (a) sc-RNAseq data, (b) serial biological replicate samples from the same patients taken several weeks apart and (c) clinical response annotations from a retrospective collection of samples. This effort will establish the foundation for an expanded effort to ultimately make it possible for fresh tissues from multiple human diseases to be compatible with functional genomics research.

Here Applicants proposed a pilot of a "living biosensors" pipeline to use label-free imaging to predict cell types and drug-induced death states in freshly procured cancer, tissue, and other cell samples with an initial focus on gastroesophageal ascites.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of identifying cell types and/or cell phenotypes in an ex vivo sample comprising:
   (a) distributing sub-samples of a cancer sample obtained from a subject into individual discrete volumes, wherein each individual discrete volume comprises a mixture of cells;
   (b) obtaining one or more label-free images of the mixture of cells in each individual discrete volume;
   (c) identifying cancer cells in each individual discrete volume using a morphological classifier previously trained to identify cancer cells in a sample comprising a mixture of cells;
   (d) exposing each individual discrete volume to a different treatment, wherein each treatment comprises one or more drugs or a variable concentration of one or more drugs;
   (e) obtaining multiple label-free images of the mixture of cells in each individual discrete volume at multiple time points, and
   (f) identifying the cancer cells as sensitive or resistant to a given treatment using a convolutional neural network previously trained to extract one or more morphological features of the identified cancer cells from the obtained multiple label-free images and identify cancer cell sensitivity or resistance based on the extracted one or more morphological features, wherein identifying if the cancer cells are sensitive or resistant to the treatment comprises distinguishing between drug-induced cell death and non-drug-induced cell death.

2. The method of claim 1, wherein the label-free images are obtained by transmitted-light microscopy.

3. The method of claim 1, wherein the cancer sample is aseptically collected from the subject.

4. The method of claim 1, wherein the cancer sample is fresh or is cryopreserved.

5. The method of claim 1, wherein the cancer sample is ascites fluid.

6. The method of claim 1 wherein at least one individual discrete volume is not exposed to a treatment.

7. The method of claim 1, further comprising repeating steps (a)-(f) on one or more additional samples obtained from the subject at different time points during a defined time window and identifying any change in treatment sensitivity at the different time points.

8. The method of claim 1, wherein the drug is a cytotoxic or targeted.

9. The method of claim 1, wherein the label-free imaging of each discrete volume is performed over a 24-hour period.

10. The method of claim 1, wherein the sub-samples are cultured in 2D.

11. The method of claim 1, wherein the sub-samples are cultured as a spheroid culture or on a 3D scaffold.

12. The method of claim 1, wherein the sub-samples are cultured as organoids.

13. The method of claim 7, wherein the time window is less than 10 days, less than 5 days, or less than 72 hours.

14. The method of claim 7, wherein the additional samples comprise samples obtained before the subject starting a therapeutic treatment and after completing the therapeutic treatment.

15. The method of claim 1, wherein the drug is an immunomodulating agent.

16. The method of claim 1, wherein the label-free imaging of each discrete volume is performed over a 48-hour period.

17. The method of claim 1, wherein the label-free imaging of each discrete volume is performed over a 72-hour period.

18. The method of claim 1, wherein the label-free imaging of each discrete volume is performed over a 96-hour period.

19. The method of claim 1, wherein the label-free imaging of each discrete volume is performed over a 120-hour period.

20. The method of claim 1, wherein the label-free imaging of each discrete volume is performed over a 144-hour period.

* * * * *

UNITED STATES PATENT AND TRADEMARK OFFICE
CERTIFICATE OF CORRECTION

PATENT NO. : 12,241,830 B2
APPLICATION NO. : 17/113790
DATED : March 4, 2025
INVENTOR(S) : Jesse Boehm et al.

It is certified that error appears in the above-identified patent and that said Letters Patent is hereby corrected as shown below:

On the Title Page

In Column 1, item (73), "Assignee:" Line 1, delete "Broad Institute, Inc." and insert -- The Broad institute, Inc. --.

In Column 2, item (74), "Attorney, Agent, or Firm", Line 2, delete "Nix;" and insert -- Nix, LLC; --.

In the Specification

In Column 1, Line 10, Below "incorporated herein by reference." insert -- STATEMENT REGARDING FEDERALLY SPONSORED RESEARCH
This invention was made with government support under grant number CA248280 awarded by the National Institutes of Health. The government has certain rights in the invention. --.

In Column 2, Line 9, delete "CRISPR-Cas based" and insert -- CRISPR-Cas-based --.

In Column 2, Line 11, delete "CRISPR-Cas based" and insert -- CRISPR-Cas-based --.

In Columns 2-3, Lines 67 (Column 2) – 1 (Column 3), delete "CRISPR-Cas based" and insert -- CRISPR-Cas-based --.

In Column 7, Line 8, delete "Logomorpha," and insert -- Lagomorpha, --.

In Column 7, Line 11, delete "Perssodactyla," and insert -- Perissodactyla, --.

In Column 7, Line 13, delete "Simoids" and insert -- Simians --.

Signed and Sealed this
Ninth Day of December, 2025

John A. Squires
*Director of the United States Patent and Trademark Office*

CERTIFICATE OF CORRECTION (continued)
U.S. Pat. No. 12,241,830 B2

In Column 8, Line 34, delete "perturbations," and insert -- perturbations and --.

In Column 8, Line 35, delete "markers and" and insert -- markers. --.

In Column 11, Line 51, delete "Hoescht" and insert -- Hoechst --.

In Column 15, Line 63, delete "okadic" and insert -- okadaic --.

In Column 18, Line 34, after "III-B," insert -- III-C, III-D, --.

In Column 19, Line 13, delete "Cash 1)." and insert -- Cas11). --.

In Column 21, Line 42, delete "SETT/9)," and insert -- SET7/9), --.

In Column 24, Line 36, delete "CRIPSR-Cas" and insert -- CRISPR-Cas --.

In Column 29, Line 55, delete "LbCp1" and insert -- LbCpf1 --.

In Column 30, Line 29, delete "PAM-SCNAR" and insert -- PAM-SCANR --.

In Column 30, Line 34, delete "Instead" and insert -- Instead, --.

In Column 41, Line 53, delete "and or" and insert -- and/or --.

In Column 45, Line 3, delete "entirety" and insert -- entirety. --.

In Column 45, Line 32, delete "Nature523," and insert -- Nature 523, --.

In Column 53, Lines 15-16, delete "pregeletanized" and insert -- pregelatinized --.

In Column 53, Line 67, delete "diagnostic," and insert -- diagnostic. --.

In the Claims

In Column 67, Line 7, in Claim 8, delete "targeted." and insert -- targeted agent. --.